United States Patent
Mitsuzuka et al.

(10) Patent No.: US 6,515,050 B1
(45) Date of Patent: Feb. 4, 2003

(54) COMB-SHAPED DIOL, WATER-SOLUBLE POLYURETHANE, AND APPLICATION THEREOF

(75) Inventors: Masahiko Mitsuzuka, Sodegaura (JP); Manabu Tsuruta, Sodegaura (JP); Yunzhi Wu, Sodegaura (JP)

(73) Assignee: Mitsui Chemicals, Inc., Tokyo (JP)

( * ) Notice: Subject to any disclaimer, the term of this patent is extended or adjusted under 35 U.S.C. 154(b) by 0 days.

(21) Appl. No.: 09/763,754

(22) PCT Filed: Oct. 13, 2000

(86) PCT No.: PCT/JP00/07127

§ 371 (c)(1),
(2), (4) Date: Feb. 27, 2001

(87) PCT Pub. No.: WO01/77066

PCT Pub. Date: Oct. 18, 2001

(30) Foreign Application Priority Data

Apr. 7, 2000 (JP) ........................................ 2000-105865

(51) Int. Cl.[7] ................................................ C08L 1/26
(52) U.S. Cl. ........................................ 524/44; 568/704
(58) Field of Search ............................... 528/44; 568/704

(56) References Cited

U.S. PATENT DOCUMENTS

| 3,926,867 A | * 12/1975 | Quock ..................... 260/2.5 |
| 4,048,100 A | * 9/1977 | Gurgiolo .................. 260/2.5 |
| 4,275,236 A | 6/1981 | Earl et al. |
| 4,281,201 A | 7/1981 | Abend |
| 4,311,692 A | 1/1982 | Abend |
| 4,426,485 A | 1/1984 | Hoy et al. |
| 4,826,921 A | * 5/1989 | Andrews ................... 525/102 |

FOREIGN PATENT DOCUMENTS

| DE | A1-3012765 | 10/1981 |
| JP | B437134 | 9/1960 |
| JP | A57123850 | 8/1982 |
| JP | A5978226 | 5/1984 |
| JP | A10298261 | 11/1998 |

* cited by examiner

*Primary Examiner*—Edward J. Cain
(74) *Attorney, Agent, or Firm*—Birch, Stewart, Kolasch & Birch, LLP

(57) ABSTRACT

A water-soluble polyurethane obtained from water-soluble polyalkylene glycol, polydiisocyanate, and comb-shaped hydrophobic diol represented by the following general formula:

$$R^2\text{-}(O\text{-}X)_n\text{-}Z\diagup\underset{\underset{(X''\text{-}O)_k\text{-}R^1}{|}}{\overset{\overset{OH\diagdown N\diagup OH}{|}}{R^4}}\diagdown Z'\text{-}(X'\text{-}O)_{n'}\text{-}R^3 \quad (1)$$

wherein $R^1$ is a hydrocarbon group of 1 to 20 carbon atoms; each of $R^2$ and $R^3$ is a hydrocarbon group or halogenated hydrocarbon group of 4 to 21 carbon atoms; each of X, X' and X" is an alkylene group of 2 to 10 carbon atoms; the hydrogen atoms of the above alkylene group may be substituted with an alkyl group, chlorine or an alkyl chloride group; each of Z and Z' is oxygen, sulfur or a $CH_2$ group; $R^4$ is an alkylene group of 2 to 10 carbon atoms in all; k is an integer of 0 to 15; n is an integer of 0 to 15 when Z is oxygen and is 0 when Z is sulfur or a $CH_2$ group; n' is an integer of 0 to 15 when Z' is oxygen and is 0 when Z' is sulfur or a $CH_2$ group. The water-soluble polyurethane is used as, for example, an extruding auxiliary for use in cement-based materials, a mortar thickening agent, a thickening agent for underwater concrete, a ceramics forming binder and a moisturizer for hair cosmetics, all of which are characterized by low tackiness and high shape retention.

35 Claims, 3 Drawing Sheets

COMB-SHAPED DIOL, WATER-SOLUBLE POLYURETHANE, AND APPLICATION THEREOF

This application is the national phase under 35 U.S.C. §371 of PCT International Application No. PCT/JP00/07127 which has an International filing date of Oct. 13, 2000, which designated the United States of America.

BACKGROUND OF THE INVENTION

1. Field of the Invention

The present invention relates to novel diol compounds each having a comb-shaped structure, novel water-soluble polyurethane obtained using thereof, and usages of the water-soluble polyurethane.

The present invention also relates to an extruding auxiliary using the above novel water-soluble polyurethane, an extruding composition of a cement material containing the extruding auxiliary, and extruded articles of a cement material having improved strength obtained by extruding the above extruding composition of a cement material. The present invention further relates to a novel thickening agent for a mortar available for widely varying types of mortar such as repairing mortar, tile-bonding mortar, masonry mortar, spraying mortar, substrate mortar and topping mortar. The present invention further relates to a novel thickening agent for an underwater concrete and a composition for at underwater concrete containing the novel thickening agent for an underwater concrete. The present invention further relates to a novel ceramics forming binder. And the present invention further relates to a novel moisturizer for hair cosmetics excellent in moisture retention to hair.

2. Related Arts

When extruding a mortar comprising a cement, a fine aggregate, a fiber and water with a vacuum extruder or the like to produce cement plates extruding the same, in order to extrude the mortar without separating water therefrom, in other words, in order to impart water retention to the mortar, there has been a need to add a water-soluble polymer to the mortar (refer to, for example, Japanese Patent Publication No. 43-7134). In order to develop sufficient water retention, the aqueous mortar solution needs to have a high viscosity, and water-soluble cellulose ethers such as methyl cellulose (MC), hydroxypropyl methyl cellulose (HPMC) and hydroxyethyl cellulose (HEC) are mainly used as the water-soluble polymer at present.

In order to retain the shape of extruded articles immediately after extrusion, in other words, in order to impart shape retention to mortar, the mortar needs to exhibit excellent thixotropic properties; and, it was not sufficient to impart shape retention thereto by an addition of only the water-soluble polymer such as methyl cellulose to the mortar. Thus, asbestos has been used in combination with water-soluble cellulose ethers (refer to, for example, Japanese Patent Publication No. 43-7134).

So, in the conventional extrusion process, the requirements of water retention and shape retention of mortar in extruding mortar have been satisfied by the use of asbestos in combination with water-soluble cellulose ethers.

In recent years, however, the harmfulness of asbestos has been pointed out and restrictions have been imposed on its use. As a result, the fibers such as various types of polymer fibers and glass fibers have become in use as substitutes for asbestos. The mortar using these asbestos-substitute fibers is, however, inferior in shape retention to the mortar using asbestos. Thus, there have been demands for the development of novel extruding auxiliary capable of imparting water retention as well as sufficient shape retention to mortar with the use of asbestos-substitute fibers.

On the other hand, the water-soluble cellulose ethers have a problem that they are likely to trap bubbles when mixing mortar, and due to the bubbles, the strength of the extruded articles of the mortar is likely to decrease.

In addition, the water-soluble cellulose ethers are relatively expensive because they are semisynthetic polymers produced from special natural wood pulp as a raw material and boost the raw material costs of the extruded articles. Furthermore, the natural wood pulp as resources is limited. Thus, a novel extruding auxiliary has been desired which can be synthesized from less expensive industrial materials.

In the forming of ceramics, particularly in extrusion of ceramics, an extruding binder composed of a water-soluble polymer is blended so as to impart sufficient plasticity, tackiness and lubricating properties to the green sand, and various types of cellulose ethers such as methyl cellulose (MC) and hydroxypropyl methyl cellulose (HPMC) are widely used as the polymers.

The cellulose ethers, however, have a problem that their heat release in degreasing is rapid and the heat release value is high, therefore, the extruded articles are likely to be damaged at the time of degreasing. Furthermore, it is also a problem that carbonized residues or carbonized inorganic salts are likely to remain after degreasing (high carbon residue content).

Hair cosmetics such as hair conditioner, hair gel, hair foam, shampoo and rinse require moisturizer, which contains water-soluble polymer, so as to create moist feel. And, as the polymers for such cosmetics, water-soluble polymers such as polyethylene glycol (PEG) or various types of cellulose ethers are widely used at present.

However, for polyethylene glycol, it has a problem of creating a sticky hair impression, but not creating moist feel. At the same time, cellulose ethers such as hydroxyethyl cellulose (HEC) also have a problem of creating a stiffed hair impression, but not creating moist feel.

SUMMARY OF THE INVENTION

Accordingly, an object of the present invention is to provide novel diol compounds each having a comb-shaped structure and novel water-soluble polyurethane using thereof.

Another object of the present invention is to provide a novel extruding auxiliary as a replacement of water-soluble cellulose ethers, and which is more economical and is capable of imparting excellent shape retention to mortar, imparting excellent strength to the extruded articles of the mortar, and imparting improved formability to mortar. Still another object of the present invention is to provide an extruding composition of cement-based material which has excellent shape retention, of which extruded articles have excellent strength, and of which formability has been improved, and extruded articles of cement-based material of which strength has been improved.

Still another object of the present invention is to provide a novel mortar thickening agent which is available for widely varying types of mortar such as repairing mortar, tile-bonding mortar, masonry mortar, spraying mortar, bedding mortar and facing mortar.

Further object of the present invention is to provide a novel thickening agent for underwater concrete as a replacement of water-soluble cellulose ethers, and which is more economical and excellent in underwater anti-separating properties, and is improved retardation of setting.

Still further object of the present invention is to provide a novel ceramics forming binder to replace cellulose ethers whose heat release in degreasing is slow, heat release value is low, and carbon residue content is also low.

Yet another object of the present invention is to provide a novel moisturizer for a hair cosmetic as a replacement of PEG or cellulose ethers, and which imparts water retention to hair and creates excellent moist hair impression.

After concentrating our energies on solving the afore-described problems, we, the present inventors found that the above-described properties such as water retention and formability can be attained by improving the structure of comb-shaped diol as a raw material of water-soluble polyurethane, and on the basis of this acknowlegement we finally thought out the present invention.

Specifically, the present invention with which the above objects can be achieved is a comb-shaped diol represented by the following general formula (1):

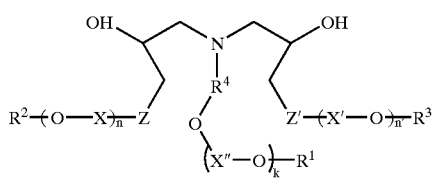

(1)

wherein $R^1$ is a hydrocarbon group of 1 to 20 carbon atoms; each of $R^2$ and $R^3$ is a hydrocarbon group of 4 to 21 carbon atoms; some or all of the hydrogen atoms of the hydrocarbon groups $R^1$, $R^2$ and $R^3$ may be substituted with fluorine, chlorine, bromine or iodine; $R^2$ and $R^3$ may be the same or different from each other; each of X, X' and X" is an alkylene group of 2 to 10 carbon atoms; X, X'and X" may be the same or different from each other; some of the hydrogen atoms of the above alkylene group may be substituted with an alkyl group, chlorine or an alkyl chloride group; each of Z and Z' is oxygen, sulfur or a $CH_2$ group; Z and Z' may be the same or different from each other; $R^4$ is an alkylene group of 2 to 10 carbon atoms in all; k is an integer of 0 to 15; n is an integer of 0 to 15 when Z is oxygen and is 0 when Z is sulfur or a $CH_2$ group; n' is an integer of 0 to 15 when Z' is oxygen and is 0 when Z' is sulfur or a $CH_2$ group; and n and n' may be the same or different from each other.

In an embodiment of the present invention, the comb-shaped diol includes a diol represented by the following general formula (1a):

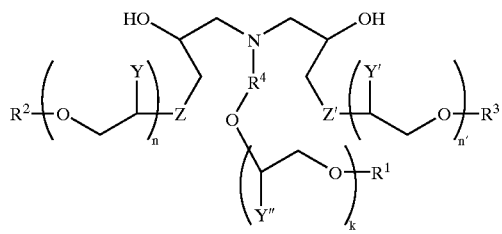

(1a)

wherein $R^1$ is a hydrocarbon group of 1 to 20 carbon atoms; each of $R^2$ and $R^3$ is a hydrocarbon group of 4 to 21 carbon atoms; some or all of the hydrogen atoms of the hydrocarbon groups $R^1$, $R^2$ and $R^3$ may be substituted with fluorine, chlorine, bromine or iodine; $R^2$ and $R^3$ may be the same or different from each other; each of Y, Y' and Y" is hydrogen, a methyl group or a $CH_2Cl$ group; Y and Y' may be the same or different from each other; each of Z and Z' is oxygen, sulfur or a $CH_2$ group; Z and Z' may be the same or different from each other; $R^4$ is an alkylene group of 2 to 4 carbon atoms in all; k is an integer of 0 to 15; n is an integer of 0 to 15 when Z is oxygen and is 0 when Z is sulfur or a $CH_2$ group; n' is an integer of 0 to 15 when Z' is oxygen and is 0 when Z' is sulfur or a $CH_2$ group; and n and n' may be the same or different from each other.

Further, in a preferred embodiment of the present invention, the comb-shaped diol includes a diol represented by the following general formula (2):

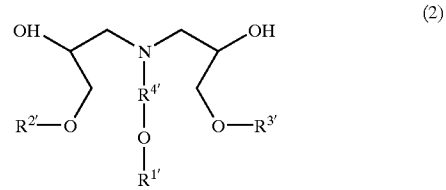

(2)

wherein $R^1$ is an alkyl group of 1 to 18 carbon atoms; each of $R^{2'}$ and $R^{3'}$ is a hydrocarbon group of 4 to 21 carbon atoms; $R^{2'}$ and $R^{3'}$ are the same; $R^{4'}$ is a 1,2-ethylene group, 1,3-propylene group or 1,4-butylene group.

The present invention is also directed to a water-soluble polyurethane, which comprise a polymer having a repeating unit (U-1) represented by the following general formula (3):

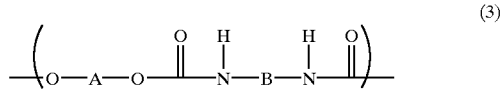

(3)

and a repeating unit (U-2) represented by the following general formula (4):

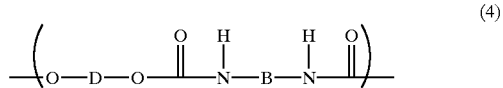

(4)

wherein A is a bivalent group derived from a water-soluble polyalkylene polyol (hereinafter referred to as compound A), wherein the compound A having a general formula HO—A—OH, having hydroxyl groups at least on both terminals thereof and having a number average molecular weight of 400 to 100,000; B is a bivalent group derived from a polyisocyanate compound (hereinafter referred to as compound B), wherein the compound B being selected from the group consisting of polyisocyanates represented by a general formula OCN—B—NCO and having 3 to 18 carbon atoms; and D is a bivalent group such that the compounds having a general formula HO—D—OH is comb-shaped diol having the above-described general formula (1) (hereinafter referred to as compound D);

wherein the molar ratio of the repeating unit (U-1) being 0.5 or higher and 0.999 or lower, the molar ratio of the repeating unit (U-2) being 0.001 or higher and 0.5 or lower, the weight average molecular weight measured by the GPC being in the range of 10,000 to 10,000,000.

In a preferred embodiment of the water-soluble polyurethane according to the present invention, the molar ratio of the repeating unit (U-1) is 0.5 or higher and 0.99 or lower, the molar ratio of the repeating unit (U-2) is 0.01 or higher and 0.5 or lower, the above compound A is a polyethylene glycol of which number average molecular weight is 3,000 to 20,000, the above compound B is a diisocyanate compound selected from the group consisting of aliphatic diisocyanates of which total number of carbon atoms is 3 to 18, the above compound D is the comb-shaped diol having the above general formula (2), and the water-soluble polyurethane has a weight average molecular weight, as measured by GPC, being in the range of 100,000 to 1,000,000.

The present invention is also directed to the water-soluble polyurethane, wherein the above compound B is hexamethylene diisocyanate, isophoronediisocyanate, hydrogenated xylylenediisocyanate, hydrogenated tolylene diisocyanate, or norbornanediisocyanatomethyl.

The present invention with which the above objects can be achieved is further directed to an extruding auxiliary for a cement material, which comprises a water soluble polyurethane having a repeating unit (U-1) represented by the above described general formula (3) and a repeating unit (U-2) represented by the above described general formula (4), and wherein 2.5% aqueous solution of the polyurethane has a viscosity of 1,000 to 1,000,000 mPa·s.

The present invention is also directed to an extruding composition of a cement material which comprises hydraulic inorganic powder, fine aggregate, fiber, the above extruding auxiliary and water.

Further, the present invention is directed to the extruding composition of cement material wherein asbestos-substitute fiber is used as the fiber.

The present invention is also directed to an extruded article of cement material which is obtained by extruding the above extruding composition and thus having an improved strength.

The present invention with which the above objects can be achieved also directed to a mortar thickening agent which comprise a water-soluble polyurethane having a repeating unit (U-1) represented by the above-described general formula (3) and a repeating unit (U-2) represented by the above-described general formula (4), the molar ratio of the repeating unit (U-1) being 0.5 or higher and 0.99 or lower, the molar ratio of the repeating unit (U-2) being 0.01 or higher and 0.5 or lower, and wherein 2% aqueous solution of the polyurethane has a viscosity being in the range of 10 mPa·s to 300,000 mPa·s at 20° C.

Further, the present invention is directed to the mortar thickening agent, wherein the above-described compound A, which is a constituent of the above-described polymer, is polyethylene glycol having a number average molecular weight being in the range of 1,000 to 20,000.

Still further, the present invention is directed to the mortar thickening agent, wherein the above-described compound B, which is a constituent of the above-described polymer, is a chain aliphatic diisocyanate or cyclic aliphatic diisocyanate.

In a preferred embodiment of the mortar thickening agent according to the present invention, the above-described compound B is hexamethylene diisocyanate, isophoronediisocyanate, hydrogenated tolylenediisocyanate, hydrogenated xylylenediisocyanate, or norbornanediisocyanatomethyl.

In another preferred embodiment of the mortar thickening agent according to the present invention, the above-described compound D is a comb-shaped diol represented by the above general formula (1a), and more preferably a comb-shaped diol represented by the above general formula (2).

The present invention is also directed to a dry mortar composition which comprises hydraulic inorganic powder and the above-described mortar thickening agent.

The present invention is also directed to a mortar composition which comprises hydraulic inorganic powder, water and the above mortar thickening agent.

Furthermore, the present invention with which the above objects can be achieved is directed a thickening agent for underwater concrete which comprises a water-soluble polyurethane having a repeating unit (U-1)represented by the above-described general formula (3) and a repeating unit (U-2) represented by the above-described general formula (4), the molar ratio of the repeating unit (U-1) being 0.5 or higher and 0.99 or lower, the molar ratio of the repeating unit (U-2) being 0.01 or higher and 0.5 or lower, and wherein the polyurethane has a weight average molecular weight, as measured by the GPC, being in the range of 100,000 to 1,000,000.

In a preferred embodiment of the underwater concrete thickening agent according to the present invention, the compound D is a comb-shaped diol represented by the above general formula (1a), and more preferably a comb-shaped hydrophobic diol represented by the above general formula (2).

The present invention is also directed to the underwater concrete thickening agent, wherein the above-described compound B, which is a constituent of the above-described polymer, is chain aliphatic diisocyanate or cyclic aliphatic diisocyanate.

In a preferred embodiment of the underwater concrete thickening agent according to the present invention, the compound B is hexamethylene diisocyanate, isophoronediisocyanate, hydrogenated tolylenediisocyanate, hydrogenated xylylenediisocyanate, or norbornanediisocyanatomethyl.

In a preferred embodiment of the underwater concrete thickening agent according to the present invention, 2% aqueous solution of the water-soluble polyurethane has a viscosity being in the range of 1,000 mPa·s to 500,000 mPa·s.

The present invention with which the above objects can be achieved is also directed to an underwater concrete composition which comprises cement and the above underwater concrete thickening agent wherein the thickening agent is added at the rate of 0.1 to 10% by weight on the basis of 100% by weight of the cement.

The present invention is also directed to a ceramics forming binder which comprises a water-soluble polyurethane having a repeating unit (U-1) represented by the above-described general formula (3) and a repeating unit (U-2) represented by the above-described general formula (4), the molar ratio of the repeating unit (U-1) being 0.5 or higher and 0.99 or lower, the molar ratio of the repeating unit (U-2) being 0.01 or higher and 0.5 or lower, and wherein the polyurethane having a weight average molecular weight, as measured by the GPC, being in the range of 10,000 to 1,000,000.

In a preferred embodiment of ceramics forming binder according to the present invention, the compound D is a comb-shaped hydrophobic diol represented by the above general formula (1a), and more preferably a comb-shaped diol represented by the above general formula (2).

The present invention is also directed to the ceramics forming binder wherein the compound A, which is a constituent of the above-described polymer, is polyethylene glycol of which number average molecular weight is 1,000 to 20,000 and the compound B is a chain aliphatic diisocyanate or cyclic aliphatic diisocyanate.

In a preferred embodiment of ceramics forming binder according to the present invention, the compound B is hexamethylene diisocyanate, isophoronediisocyanate, hydrogenated tolylenediisocyanate, hydrogenated xylylenediisocyanate, or norbornanediisocyanatomethyl.

The ceramics forming binder of the present invention is preferably used as a binder for ceramics extrusion.

The present invention is also directed to a moisturizer for hair cosmetics which comprises a water-soluble polyurethane having a repeating unit (U-1) represented by the above-described general formula (3) and a repeating unit (U-2) represented by the above-described general formula (4), the molar ratio of the repeating unit (U-1) being 0.5 or higher and 0.99 or lower, the molar ratio of the repeating unit (U-2) being 0.01 or higher and 0.5 or lower, and the polyurethane having a weight average molecular weight, as measured by the GPC, being in the range of 10,000 to 1,000,000.

In a preferred embodiment of moisturizer for hair cosmetics according to the present invention, the above-described compound D is a comb-shaped diol represented by the above general formula (1a), and more preferably a comb-shaped diol represented by the above general formula (2).

The present invention is also directed to the moisturizer for hair cosmetics wherein the compound A, which is a constituent of the above-described polymer, is polyethylene glycol of which number average molecular weight is 400 to 20,000 and the compound B is a chain aliphatic diisocyanate or cyclic aliphatic diisocyanate.

In a preferred embodiment of moisturizer for use in hair cosmetics according to the present invention, the compound B is hexamethylene diisocyanate, isophoronediisocyanate, hydrogenated tolylenediisocyanate, hydrogenated xylylenediisocyanate, or norbornanediisocyanatomethyl.

BRIEF DESCRIPTION OF THE DRAWINGS

In FIG. 1, a broken line denoted by reference numeral 1 shows the viscosity of the mortar obtained in the comparative example 9 described later, a dotted line denoted by reference numeral 2 the viscosity of the mortar obtained in the comparative example 10 described later, a dashed line denoted by reference numeral 3 the viscosity of the mortar obtained in the example 37 described later, a solid line denoted by reference numeral 4 the viscosity of the mortar obtained in the example 38 described later, a broken line denoted by reference numeral 5 the viscosity of the mortar o obtained in the example 39 described later, a chain double-dashed line denoted by reference numeral 6 the viscosity of the mortar obtained in the example 40 described later.

FIG. 2a is a graphical view showing the result of TGA (thermmogravimetric analysis) measurement of the thermal decomposition behavior for a binder according to the present invention by the.

FIG. 2b is a graphical view showing the result of TGA measurement of the thermal decomposition behavior for a conventional binder.

DETAILED DESCRIPTION OF THE INVENTION

Figure 1:
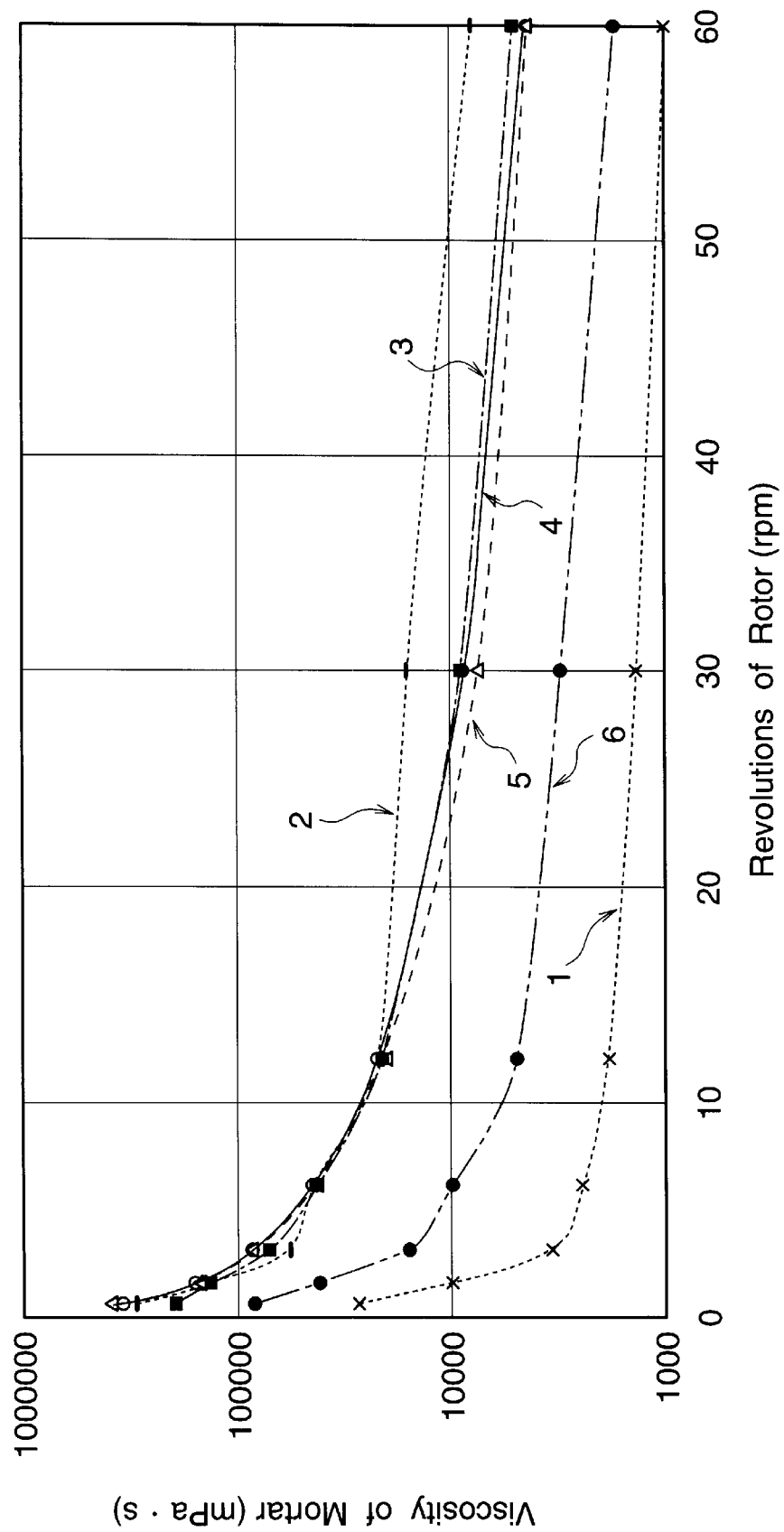
FIG. 1 is a graphical view showing the thickening effect of thickening agents according to the present invention on mortar.

Now, the present invention will be described in further detail with reference to some preferred embodiments.

Comb-shaped Diol Compound

The comb-shaped diol of the present invention (hereinafter referred to as compounds D) can be represented by the following general formula (1):

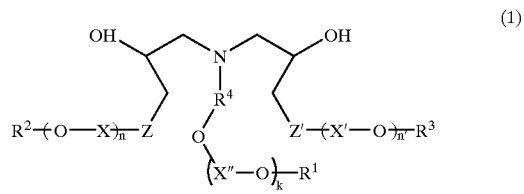

(1)

In the formula (1), $R^1$ is a hydrocarbon group, such as alkyl group, alkenyl group, aralkyl group or aryl group, having 1 to 20 carbon atoms, more preferably having 4 to 18 carbon atoms.

Each of $R^2$ and $R^3$ is a hydrocarbon group, such as alkyl group, alkenyl group, aralkyl group or aryl group, having 4 to 21 carbon atoms, more preferably having 4 to 18 carbon atoms; some or all of the hydrogen atoms of the hydrocarbon groups $R^1$, $R^2$ and $R^3$ may be substituted with halogen atoms such as fluorine, chlorine, bromine or iodine; $R^2$ and $R^3$ may be the same or different from each other, but preferably they are the same.

Each of X, X' and X" is an alkylene group of 2 to 10 carbon atoms, more preferably having 2 to 4 carbon atoms; X, X' and X" may be the same or different from each other. Some of the hydrogen atoms of the above alkylene group may be substituted with an alkyl group, chlorine or an alkyl chloride group.

$R^4$ is an alkylene group of 2 to 10 carbon atoms. In particular, the alkylene group $R^4$ includes, for example, 1,2-ethylene group, 1,3-propylene group, 1,2-propylene group, 1,4-butylene group and 2,3-butylene group.

What k stands for is an integer of 0 to 15, more preferably an integer of 0 to 5.

Each of Z and Z' is oxygen, sulfur or a $CH_2$ group, Z and Z' may be the same or different from each other, but preferably they are the same. Further, it is more preferably that both Z and Z' are oxygen.

What n stands for is an integer of 0 to 15, more preferably an integer of 0 to 5, when Z is oxygen, and is 0 when Z is sulfur or $CH_2$ group. Further, n' is an integer of 0 to 15, more preferably an integer of 0 to 5, when Z' is oxygen, and is 0 when Z' is sulfur or $CH_2$ group, and n and n' may be the same or different from each other, but preferably they are the same.

The compound D according to the present invention typically includes a comb-shaped diol represented by the following general formula (1a):

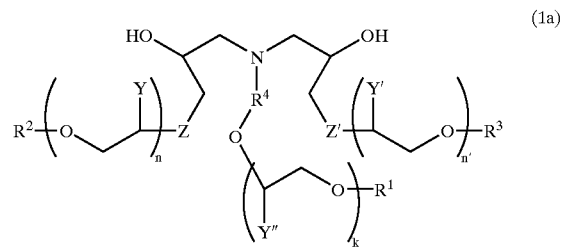

(1a)

In the general formula (1a), $R^1$ is a hydrocarbon group, such as alkyl group, alkenyl group, aralkyl group or aryl group, having 1 to 20 carbon atoms, more preferably having 4 to 18 carbon atoms.

Each of $R^2$ and $R^3$ is a hydrocarbon group, such as alkyl group, alkenyl group, aralkyl group or aryl group, having 4 to 21 carbon atoms, more preferably having 4 to 18 carbon atoms. Some or all of the hydrogen atoms of the hydrocarbon groups $R^1$, $R^2$ and $R^3$ may be substituted with halogen atoms such as fluorine, chlorine, bromine or iodine. $R^2$ and $R^3$ may be the same or different from each other, but preferably they are the same.

Each of Y, Y' and Y" is hydrogen, a methyl group or a $CH_2Cl$ group, Y and Y' may be the same or different from each other, but preferably they are the same.

$R^4$ is an alkylene group of 2 to 4 carbon atoms, k is an integer of 0 to 15, more preferably 0 to 5.

Each of Z and Z' is oxygen, sulfur or a $CH_2$ group, Z and Z' may be the same or different from each other, but more preferably they are the same, and much more preferably both Z and Z' are oxygen.

What n stands for is an integer of 0 to 15, more preferably 0 to 5 when Z is oxygen, and is 0 when Z is sulfur or a $CH_2$ group. What n' stands for is an integer of 0 to 15, more preferably 0 to 5 when Z' is oxygen, and is 0 when Z' is sulfur or a $CH_2$ group, and n and n' may be the same or different from each other, but more preferably they are the same.

A preferred form of compounds D according to the present invention is comb-shaped diol represented by the following general formula (2):

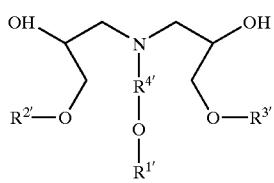
(2)

In the general formula (2), $R^{1'}$ is an alkyl group of 1 to 18 carbon atoms, more preferably of 4 to 18 carbon atoms. Each of $R^{2'}$ and $R^{3'}$ is a hydrocarbon group of 4 to 21 carbon atoms, more preferably of 4 to 18 carbon atoms, wherein $R^{2'}$ and $R^{3'}$ are the same. $R^4$ is a 1,2-ethylene group, 1,3-propylene group or 1,4-butylene group.

The comb-shaped diol (compounds D) according to the present invention is obtained by, for example, adding to primary amines having the general formula (5),

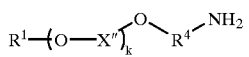
(5)

preferably primary amines having the general formula (5a),

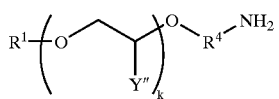
(5a)

oxirane compound having the general formula (6),

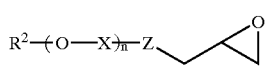
(6)

preferably oxirane compound having the general formula (6a) with the oxirane compound-to-amine ratio of 2:1 mol.

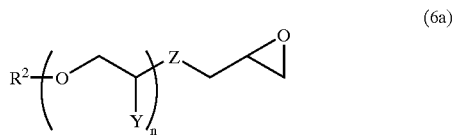
(6a)

This is expressed by the following reaction formula (7):

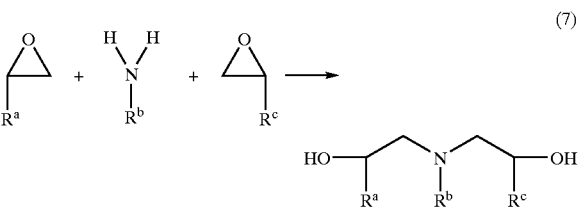
(7)

In the general formula (7), $R^b$ is a proper substituent shown in the general formula (5) or (5a) and $R^a$ and $R^c$ are proper substituents shown in the general formula (6) or (6a). In the general formulae (5) and (6), $R^1$, $R^2$, $R^4$, Z, X, X", k and n are the same as those shown in the general formula (1) and in the general formulae (5a) and (6a), $R^1$, $R^2$, $R^4$, Z, Y, Y", k and n are the same as those shown in the general formula (1a).

Specifically, the primary amines include, for example, 2-alkoxyethylamines, 3-alkoxypropylamines, 4-alkoxybutylamines, alkenyloxyalkylamines, aralkyloxyalkylamines, aryloxyalkylamines, amino alkyl ethers as alcohol-alkylene oxide addition products and amino alkyl ethers as phenol/alkyl substituted phenol-alkylene oxide addition products.

The 2-alkoxyethylamines include, for example, 2-methoxyethylamine, 2-ethoxyethylamine, 2-propoxyethylamine, 2-isopropoxyethylamine, 2-butoxyethylamine, 2-(isobutoxy)ethylamine, 2-(tert-butoxy)ethylamine, 2-pentyloxyethylamine, 2-hexyloxyethylamine, 2-heptyloxyethylamine, 2-octyloxyethylamine, 2-(2-ethylhexyloxy)ethylamine, 2-(α-butyloctyloxy)ethylamine, 2-decyloxyethylamine, 2-dodecyloxyethylamine, 2-tetradecyloxyethylamine, 2-pentadecyloxyethylamine, 2-hexadecyloxyethylamine, 2-heptadecyloxyethylamine, 2-octadecyloxyethylamine, 2-nonadecyloxyethylamine and 2-eicosyloxyethylamine.

The 3-alkoxypropylamines include, for example, 3-methoxypropylamine, 3-ethoxypropylamine, 3-propoxypropylamine, 3-isopropoxypropylamine, 3-butoxypropylamine, 3-(isobutoxy)propylamine, 3-(tert-butoxy)propylamine, 3-pentyloxypropylamine, 3-hexyloxypropylamine, 3-heptyloxypropylamine, 3-octyloxypropylamine, 3-(2-ethylhexyloxy)propylamine, 3-(α-butyloctyloxy)propylamine, 3-decyloxypropylamine, 3-dodecyloxypropylamine, 3-tetradecyloxypropylamine, 3-pentadecyloxypropylamine, 3-hexadecyloxypropylamine, 3-heptadecyloxypropylamine, 3-octadecyloxypropylamine, 3-nonadecyloxpropylamine and 3-eicosyloxpropylamine.

The 4-alkoxybutylamines include, for example, 4-methoxybutylamine, 4-ethoxybutylamine, 4-propoxybutylamine, 4-isopropoxybutylamine, 4-butoxybutylamine, 4-(isobutoxy)butylamine, 4-(tert-butoxy)butylamine, 4-pentyloxybutylamine, 4-hexyloxybutylamine, 4-heptyloxybutylamine, 4-octyloxybutylamine, 4-(2-ethylhexyloxy)butylamine, 4-(α-butyloctyloxy)butylamine, 4-decyloxybutylamine, 4-dodecyloxybutylamine, 4-tetradecyloxybutylamine, 4-pentadecyloxybutylamine, 4-hexadecyloxybutylamine, 4-heptadecyloxybutylamine, 4-octadecyloxybutylamine, 4-nonadecyloxybutylamine and 4-eicosyloxybutylamine and 4-(2,4-di-tert-amylphenoxy)butylamine.

The alkenyloxyalkylamines include, for example, 3-vinyloxypropylamine, 2-allyloxyethylamine and 3-oleyloxypropylamine.

The aralkyloxyalkylamines include, for example, 2-benzyloxyethylamine and 3-phenethyloxypropylamine.

The aryloxyalkylamines include, for example, 2-phenyloxyethylamine and 3-(p-nonylphenyloxy) propylamine.

The other amines include, for example, aminoalkyl ethers of adducts of alcohols and phenols with alkylene oxides (ethylene oxide adducts, propylene oxide adducts, epichlorohydrin adducts, etc.).

The aminoalkyl ethers of adducts of alcohol with ethylene oxide include, for example, 2-[2-(dodecyloxy)ethoxy] ethylamine and 3,6,9-trioxapentadecylamine.

Similarly, the aminoalkyl ethers of adducts of alcohols and phenols with propylene oxide, with propylene oxide/ethylene oxide and with epichlorohydrin can also be used. The number of addition k is suitably about 1 to 15 in terms of aqueous solution viscosity of polyurethane.

In addition, as the oxirane compounds, various types of glycidyl ethers, 1,2-epoxy alkanes, 1,2-epoxy alkenes and glycidyl sulfides can be used.

The glycidyl ethers include, for example, alkylglycidyl ethers, alkenylglycidyl ethers, aralkylglycidyl ethers and arylglycidyl ethers.

The alkylglycidyl ethers include, for example, n-butylglycidyl ether, sec-butylglycidyl ether, tert-butylglycidyl ether, glycidylpentyl ether, glycidylhexyl ether, glycidyloctyl ether, 2-ethylhexylglycidyl ether, 2-methyloctylglycidyl ether, glycidylnonyl ether, decylglycidyl ether, dodecylglycidyl ether, glycidyllauryl ether, glycidyltridecyl ether, glycidyltetradecyl ether, glycidylpentadecyl ether, glycidylhexadecyl ether, glycidylstearyl ether, 3-(2-(perfluorohexyl)ethoxy)-1,2-epoxypropane, and 3-(3-perfluorooctyl-2-iodopropoxy)-1,2-epoxypropane.

The alkenylglycidyl ethers include, for example, allylglycidyl ether and oleylglycidyl ether.

The aralkylglycidyl ethers include, for example, benzylglycidyl ether and phenetylglycidyl ether.

The arylglycidyl ethers include, for example, phenylglycidyl ether, 4-tert-butylphenylglycidyl ether, 2-ethylphenylglycidyl ether, 4-ethylphenylglycidyl ether, 2-methylphenylglycidyl ether, glycidyl-4-nonylphenyl ether, glycidyl-3-(pentadecadienyl)phenyl ether, 2-bisphenylglycidyl ether, benzylglycidyl ether, α-naphthylglycidyl ether and dibromophenylglycidyl ether.

The other glycidyl ethers include the glycideyl ethers of adducts of alcohols and phenols with alkylene oxides (ethylene oxide adducts, propylene oxide adducts, epichlorohydrin adducts, etc.).

The glycidyl ethers of ethylene oxide adducts are, for example, glycidyl ethers of 2-ethylhexylalcohol—ethylene oxide adduct, of lauryl alcohol—ethylene oxide adduct, of 4-tert-butylphenol—ethylene oxide adduct and of nonylphenol—ethylene oxide adduct.

In addition, the glycidyl ethers which are adducts of alcohols and phenols with propylene oxide, with propylene oxide/ethylene oxide, and with epichlorohydrin can also be used. Although the glycidyl ethers as industrial chemicals usually include glycidyl ethers of epichlorohydrin adducts as by-products, such raw materials of low purity can be used, either. The number of adducts n is suitably about 1 to 15, in terms of the aqueous solution viscosity of polyurethane.

The 1,2-epoxyalkanes and 1,2-epoxyalkenes include, for example, 1,2-epoxyhexane, 1,2-epoxyheptane, 1,2-epoxyoctane, 1,2-epoxynonane, 1,2-epoxydecane, 1,2-epoxydodecane, 1,2-epoxytetradecane, 1,2-epoxyhexadecane, 1,2-epoxyoctadecane, 1,2-epoxyeicosane, 1,2-epoxy-7-octene and 1,2-epoxy-9-decene.

The other oxirane compounds include, for example, alkylglycidyl thioethers (alkylglycidylsulfides), such as 2-ethylhexylglycidyl sulfide and decylglycidyl sulfide, and arylglycidyl thioethers (arylglycidyl sulfides) such as p-nonylphenylglycidyl sulfide.

The compounds D can be obtained by reacting the above-described amines with the above-described oxirane compounds with the amine-to-oxirane compound ratio of 1:2 molecule. When using the glycidyl ethers as the oxirane compound, the reaction is facilitated much more than when using 1,2-epoxyalkanes, 1,2-epoxyalkenes or glycidyl sulfides. This may be because the glycidyl ethers are highly reactive with the amines.

The compounds D have 3 hydrophobic chains per molecule, and allowing these hydrophobic chains to be adjacent to each other facilitates effectively the hydrophobic association among water-soluble polyurethane in aqueous solution. Each hydrophobic chain needs to have as many carbon atoms as it can have a length enough to allow the polymer to form satisfactory association. The number of carbon atoms of the amines is preferably 1 or larger and 20 or smaller. The use of the amines whose number of carbon atoms is in the above range prevents the solubility of polyurethane from decreasing. More preferably used are the chain or cyclic alkyl amines whose number of carbon atoms is 1 to 18 carbon atoms, and much more preferably the chain alkyl amines whose number of carbon atoms is 4 to 18.

The number of carbon atoms of the hydrophobic groups contained in the glycidyl ethers is preferably 4 or larger and 21 or smaller. The use of the glycidyl ethers whose hydrophobic groups have carbon atoms in the above range allows the aqueous solution viscosity of the polyurethane to be satisfactorily high and prevents the solubility of the polyurethane from decreasing. More preferably used are the alkylglycidyl ethers having straight-chain alkyl groups or branched chain alkyl groups whose number of carbon atoms is 4 to 18 as the hydrophobic groups or the arylglycidyl ethers having aromatic groups or alkyl-substituted aromatic groups whose number of carbon atoms is 6 to 18 as the hydrophobic groups.

For the same reason, the number of carbon atoms of the hydrophobic groups contained in the 1,2-epoxyalkanes, 1,2-epoxyalkenes, alkylglycidyl thioethers and arylglycidyl thioethers are preferably 4 or larger and 21 or smaller.

The larger the total number of carbon atoms of the three hydrophobic chains (the total number of carbon atoms of the substituents $R^1$, $R^2$ and $R^3$ each having the above-mentioned general formulae (1) or (1a), or the total number of carbon atoms of the substituents $R^{1'}$, $R^{2'}$ and $R^{3'}$ each having the above-mentioned general formula (2)) is, the more the polymers are likely to associate in water, therefore, the higher aqueous solution viscosity can be obtained. However, too large a total number of carbon atoms is likely to allow the solubility of the polymers in water to decrease. The total number of carbon atoms of the hydrophobic groups is preferably in the range of 12 to 40, more preferably in the range of 12 to 37, and much more preferably in the range of 12 to 28. The use of the glycidyl ethers whose hydrophobic groups have carbon atoms in the above range allows the aqueous solution viscosity of the polymers obtained to be satisfactorily high and prevents the solubility of the polyurethane in water from decreasing.

The process of preparing comb-shaped hydrophobic diols will be described below; however, it should be understood that the present invention is not intended to be limited to this specific synthetic process.

Amine and an oxirane compound, as raw materials, are prepared in a reactor equipped with a stirring apparatus, a raw material introducing mechanism and a temperature controlling mechanism and are reacted with each other at a predetermined reaction temperature while being stirred.

The reaction can be conducted without a solvent; however, commonly used solvents such as dimethylformamide (DMF) may be used.

In regard to the introduction of raw materials, the amine and the oxirane compound may be prepared at a time, or either of the amine and the oxirane compound may be prepared in the reactor first, then the rest may be introduced continuously or by steps.

The suitable reaction temperature is room temperature to about 160° C., more preferably 60° C. to 120° C.

The reaction time is about 0.5 to 10 hours, though it depends on the reaction temperature.

The dispersion degree of the diol obtained after completion of the reaction can be measured by the GPC.

The OH value can be obtained by conventional procedure.

Water-soluble Polyurethane

The polymers obtained according to the present invention are polymers having an comb-shaped hydrophobic group which is obtained by subjecting water-soluble polyalkylene polyol and comb-shaped diol having an improved structure, as described above, to linkage with polyisocyanate.

The water-soluble polyalkylene polyols (compounds A) used in the present invention are alkylene oxide polymers having hydroxyl groups at least on both ends of their polymer chains.

The use of polyalkylene polyols having 3 or more hydroxyl groups, however, is likely to decrease the solubility of their products in water. Accordingly, polyalkylene glycols, which have primary hydroxyl groups on both ends of their polymer chains, are more preferably used.

Alkylene oxides as monomers include ethylene oxide, propylene oxide, butylene oxide and epichlorohydrin; however, in order to increase the solubility of the products in water and in polar solvent, the content of ethylene oxide is preferably 40% by weight or higher, more preferably 60% by weight or higher, and particularly preferably 70% by weight to 100% by weight. The polymerization product of ethylene oxide (polyethylene glycol, hereinafter referred to as PEG) is much more preferably used.

As the aforementioned compounds A, preferably used are those with a number average molecular weight of 400 to 100,000, more preferably 1,500 to 50,000, and much more preferably 3,000 to 20,000. When the molecular weight is in this range, a product having a high reaction rate and exhibiting sufficient aqueous solution viscosity is obtained and such a product is suitably used as thickening agents. When the molecular weight is in the range of 3,000 to 20,000, products exhibiting sufficient aqueous solution viscosity are most likely to be obtained. These suitable molecular weight ranges are particularly suitable when using the obtained water-soluble polyurethane as, for example, an extruding auxiliary and an underwater concrete thickening agent.

When using the obtained water-soluble polyurethane as a mortar thickening agent and as a ceramics forming binder, the above compounds A has a number average molecular weight of preferably 1,000 to 20,000. This is because, when the molecular weight is in the range of 1,000 to 20,000, in mortar thickening agents, the products are most likely to be obtained which exhibit sufficient thickening properties and solubility and, in ceramics forming binders, the products are most likely to be obtained which exhibit sufficient plasticity, tackiness and solubility.

When using the obtained water-soluble polyurethane as a moisturizer for hair cosmetics, the above compound A has a number average molecular weight of preferably 400 to 100,000, more preferably 400 to 20,000, and much more preferably 1,000 to 20,000. This is because, when the molecular weight is in the above range, the products being excellent in water retention and being sufficient in solubility are obtained and such products are suitably used in hairdressings. When the number average molecular weight is in the range of 1,000 to 20,000, the products are most likely to be obtained which exhibit water retention and solubility adequate for hairdressings.

The polyisocyanate compounds (compounds B) used in the present invention are those having 3 to 18 carbon atoms (including the carbons of NCO groups) and selected from the group consisting of chain aliphatic polyisocyanates, alicyclic polyisocyanates and aromatic polyisocyanates. When the total number of carbon atoms of polyisocyanates is in this range, the solubility of the polymer obtained becomes satisfactory.

When the polyisocyanates having 3 or more NCO groups per molecule is used, however, the solubility of the products in water is likely to decrease. Accordingly, diisocyanates which have 2 NCO groups per molecule are preferably used as polyisocyanate compounds B.

In the reaction of diisocyanates with polyalkylene glycols, the reactivity of aromatic diisocyanates, chain aliphatic diisocyanates and alicyclic diisocyanates deceases in this order. However, since aromatic diisocyanate reacts so rapidly when conducting the reaction without solvent, their reaction tends to be non-uniform; thus it tends to be difficult to control the molecular weight of aromatic diisocyanates.

The polymers produced by using aromatic diisocyanates may change with time in mortar which is highly basic, and their effect as an auxiliary may decrease with time after mixing. The reason may be that, since mortar is a strong alkali whose pH value is about 14, the bond, which are susceptible to alkali hydrolysis, between aromatic diisocyanates and polyalkylene glycols is broken.

In chain aliphatic diisocyanates and alicyclic diisocyanates, their carbon residue content in degreasing is low compared with an aromatic diisocyanate; accordingly, when using the obtained polymers as, for example, a binder for ceramics forming, they are more preferably used than aromatic diisocyanates.

Further, since chain aliphatic diisocyanates and alicyclic diisocyanates are less irritant than aromatic diisocyanates, they are usable for a moisturizer used in hair cosmetics.

Thus, aliphatic diisocyanates (chain aliphatic diisocyanates and alicyclic diisocyanates) having 3 to 18 carbon atoms in total are preferably used. And more preferably used are hexamethylene diisocyanate (known as HDI in a shortened form), isophoronediisocyanate (known as IPDI in a shortened form), hydrogenated xylylenediisocyanate (known as HXDI in a shortened form), hydrogenated tolylenediisocyanate (known as HTDI in a shortened form) or norbornanediisocyanatomethyl (known as NBDI in a shortened form). Of all the above, HDI is particularly preferably used.

Chain aliphatic diisocyanates are diisocyanate compounds having a structure in which the two NCO groups are linked with a straight-chain or branched chain alkylene group. They include, for example, methylene diisocyanate, ethylene diisocyanate, trimethylene diisocyanate, 1-methylethylene diisocyanate, tetramethylene diisocyanate, pentamethylene diisocyanate, 2-methylbutane-1,4-diisocyanate, hexamethylene diisocyanate (HDI), heptamethylene diisocyanate, 2,2'-dimethylpentane-1,5-diisocyanate, lysine diisocyanate methyl ester (LDI), octamethylene diisocyanate, 2,5-dimethylhexane-1,6-diisocyanate, 2,2,4-trimethylpentane-1,5-diisocyanate, nonamethyl diisocyanate, 2,4,4-trimethylhexane-1,6-diisocyanate, decamethylene diisocyanate, undecamethylene diisocyanate, dodecamethylene diisocyanate, tridecamethylene diisocyanate, tetradecamethylene diisocyanate, pentadecamethylene diisocyanate, hexadecamethylene diisocyanate, trimethylhexamethylene diisocyanate.

Alicyclic diisocyanates are diisocyanate compounds having a structure in which the two NCO groups are linked with an alkylene group having a cyclic structure. They include, for example, cyclohexane-1,2-diisocyanate, cyclohexane-1,3-diisocyanate, cyclohexane-1,4-diisocyanate, 1-methylcyclohexane-2,4-diisocyanate, 1-methylcyclohexane-2,6-diisocyanate, 1-ethylcyclohexane-2,4-diisocyanate, 4,5-dimethylcyclohexane-1,3-diisocyanate, 1,2-dimethylcyclohexane-ω, ω'-diisocyanate, 1,4-dimethylcyclohexane-ω, ω'-diisocyanate, isophoronediisocyanate (IPDI), dicyclohexylmethane-4,4'-diisocyanate, dicyclohexylmethylmethane-4,4'-diisocyanate, dicyclohexyldimethylmethane-4,4'-diisocyanate, 2,2'-dimethyldicyclohexylmethane-4,4'-diisocyanate, 3,3'-dimethyldicyclohexylmethane-4,4'-diisocyanate, 4,4'-methylene-bis(isocyanatocyclohexane), isopropylidenebis(4-cyclohexylisocyanate) (IPCI), 1,3-bis(isocyanatomethyl)cyclohexane, hydrogenated tolylenediisocyanate (HTDI), hydrogenated 4,4'-diphenylmethane diisocyanate (HMDI), hydrogenated xylylenediisocyanate (HXDI), and norbornane diisocyanatomethyl (NBDI).

Aromatic diisocyanates are diisocyanate compounds having a structure in which the two NCO groups are linked with an aromatic group such as phenylene group, alkyl-substituted phenylene group and aralkylene group or a hydrocarbon group containing an aromatic group. They include, for example, 1,3- and 1,4-phenylene diisocyanate, 1-methyl-2,4-phenylene diisocyanate (2,4-TDI), 1-methyl-2,6-phenylene diisocyanate (2,6-TDI), 1-methyl-2,5-phenylene diisocyanate, 1-methyl-3,5-phenylene diisocyanate, 1-ethyl-2,4-phenylene diisocyanate, 1-isopropyl-2,4-phenylene diisocyanate, 1,3-dimethyl-2,4-phenylene diisocyanate, 1,3-dimethyl-4,6-phenylene diisocyanate, 1,4-dimethyl-2,5-phenylene diisocyanate, m-xylene diisocyanate, diethylbenzene diisocyanate, diisopropylbenzene diisocyanate, 1-methyl-3,5-diethylbenzene-2,4-diisocyanate, 3-methyl-1,5-diethylbenzene-2,4-diisocyanate, 1,3,5-triethylbenzene-2,4-diisocyanate, naphthaline-1,4-diisocyanate, naphthaline-1,5-diisocyanate, 1-methylnaphthaline-1,5-diisocyanate, naphthaline-2,6-diisocyanate, naphthaline-2,7-diisocyanate, 1,1-dinaphthyl-2,2'-diisocyanate, biphenyl-2,4'-diisocyanate, biphenyl-4,4'-diisocyanate, 1,3-bis(1-isocyanato-1-methylethyl)benzene, 3,3'-dimethylbiphenyl-4,4'-diisocyanate, diphenylmethane-4,4'-diisocyanate (MDI), diphenylmethane-2,2'-diisocyanate, diphenylmethane-2,4'-diisocyanate and xylene diisocyanate (XDI).

The other polyisocyanates include, for example, 1,6,11-undeca triisocyanate, 1,8-diisocyanate-4-isocyanatemethyl octane and 1,3,6-hexamethylene triisocyanate.

The water-soluble polyurethane having a comb-shaped hydrophobic group is synthesized by the reaction of the two hydroxyl groups of polyalkylene glycol (compound A) and comb-shaped hydrophobic diol (compound D) with the two NCO groups of diisocyanate compound (compound B), as shown by the following general formula (8):

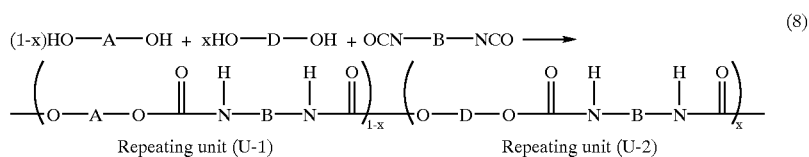

(8)

The water-soluble polyurethane whose repeating unit (U-1) has a molar ratio of (1−x) and whose repeating unit (U-2) has a molar ratio of x is obtained by conducting the above reaction at compound A to compound D molar ratio of (1−x):x.

Now the process of producing the water-soluble polyurethane will be described while giving an example; however, it should be understood that the present invention is not intended to be limited to the specific example.

The contents of a reactor equipped with a stirring apparatus, a raw material introducing mechanism and a temperature controlling mechanism is replaced with an inert gas, first. Polyalkylene glycol is prepared in the reactor. According to the situation, a solvent is also prepared in the reactor.

A catalyst is added while controlling the temperature of the reactor at a set reaction temperature. A diisocyanate compound and comb-shaped hydrophobic diol are introduced into the reactor while stirring the contents of the reactor. The way of introducing them is not limited to any specific one. They may be introduced continuously or intermittently. And the diisocyanate compound and comb-shaped hydrophobic diol may be introduced at a time or may be introduced one at a time in this order or in reverse order.

The catalyst is not necessarily added to the polyalkylene glycol before the reaction. It is possible to add the catalyst after adding the diisocyanate compound and comb-shaped hydrophobic diol to the polyalkylene glycol and then start the reaction. Alternatively it is possible to add the catalyst to the diisocyanate compound and comb-shaped hydrophobic diol previously, add these to the polyalkylene glycol, and then start the reaction.

After the set reaction time, the product is taken from the reactor and processed to finished goods in the form of pellets, flakes, powder or solution.

The catalyst used in the reaction is not limited to any specific one, the known catalysts, such as organic metal compounds, metal salts, tertiary amines, and other basic catalysts and acid catalysts, which are commonly used in the reaction of isocyanates with polyols can also be used. Those catalysts include, for example, dibutyl tin dilaurate (hereinafter referred to as DBTDL for short), dibutyl tin di(dodecilthiolate), tin octanoate, phenyl mercury acetate, zinc octoate, lead octoate, zinc naphthenate, lead naphthenate, triethylamine (TEA), tetramethylbutane diamine (TMBDA), N-ethyl morpholine (NEM), 1,4-diaza [2.2.2]bicyclo octane (DABCO), 1,8-diazabicyclo[5.4.0]-7-undecene (DBU) and N,N'-dimethyl-1,4-diazacyclohexane (DMP). Of all the above DBTDL is preferably used.

The amount of catalyst used in the reaction varies depending on the reaction temperature and type of catalyst and is not limited to any specific amount. For example, however, 0.0001 to 0.1 mol of catalyst is sufficient for 1 mol of polyalkylene glycol, more preferably about 0.001 to 0.1 mol of catalyst is used for 1 mol of polyalkylene glycol.

The reaction can be conducted without a solvent; however, it can also be conducted with a solvent so as to decrease the melting viscosity of the product. As a solvent, the solvents having no active hydrogen are effectively used. Those solvents include, for example, halogen solvents such as carbon tetrachloride, dichloromethane, chloroform and trichlene; aromatic solvents such as xylene, toluene and benzene; saturated hydrocarbon solvents such as decane, octane, heptane, hexane, cyclohexane and pentane; ether solvents such as dioxane, tetrahydrofuran, diethyl ether, dimethyl ether and ethylene glycol dimethyl ether; ketone solvents such as diethyl ketone, methyl ethyl ketone and dimethyl ketone; and ester solvents such as ethyl acetate and methyl acetate.

The process to conduct the reaction without a solvent is advantageous in terms of production costs, since it does not require the step of desolvation. And such a process is preferably used, since it is unlikely to cause environmental pollution.

The amount of diisocyanate compounds used for the reaction varies a little depending on the applications for the polymer obtained; however, in the applications to extruding auxiliaries and underwater concrete thickening agents, the amount of diisocyanate compounds per 1 mol of polyalkylene glycol plus comb-shaped hydrophobic diol in total (NCO/OH) is 0.8 to 1.3 mol, more preferably 0.9 to 1.2 mol, and much more preferably 0.95 to 1.05 mol. When the number of mol (NCO/OH) is in the range of 0.8 to 1.3, the average molecular weight of the products are satisfactorily large, and hence, the satisfactorily capability as an extruding auxiliary or underwater concrete thickening agent. With respect to the applications for the mortar thickening agent, ceramics forming binder and moisturizer for use in hair cosmetics, the amount of diisocyanate compounds per 1 mol of polyalkylene glycol plus comb-shaped hydrophobic diol in total (NCO/OH) is preferably 0.7 to 1.3 mol, more preferably 0.8 to 1.2 mol. When the mol number (NCO/OH) is in the range of 0.7 to 1.3 mol, the product can have a satisfactorily large average molecular weight, its ability as a thickening agent, or ceramics forming binder becomes satisfactory. With respect to the mortar thickening agent, when the mol number (NCO/OH) is in the range of 0.7 to 1.3, the product can have a satisfactorily large average molecular weight and its ability as the thickening agent become satisfactory, and its decrease in solubility due to the crosslinking reaction does not occur.

Under the conditions that the number of mol of diisocyanate and the total number of mol of polyalkylene glycol and comb-shaped hydrophobic diol are almost the same, the product having the largest molecular weight is obtained.

However, when polyalkylene glycol and comb-shaped hydrophobic diol contain water, an excess of diisocyanate needs to be used for making up for the diisocyanate having been decomposed by water. Accordingly, a fully dried raw material is preferably used. The water content of the raw material is preferably 5,000 ppm or lower, more preferably 1,000 ppm or lower, and much more preferably 200 ppm or lower.

For the amount of comb-shaped hydrophobic diol used in the reaction, generally 0.001 to 1 mol of comb-shaped hydrophobic diol is suitably used for 1 mol of polyalkylene glycol (x is 0.001 to 0.5), though it varies depending on the molecular weight of the polyalkylene glycol and the number of carbon atoms contained in the hydrophobic groups of the comb-shaped hydrophobic diol. When the number of mol of the comb-shaped hydrophobic diol is in this range, a product is obtained which has a desired thickening effect and has its solubility satisfactorily maintained. The values in parenthesis indicates the value x in the above-described general formula (8).

When using the product in the applications such as mortar thickening agent, underwater concrete thickening agent, ceramics forming binder and moisturizer for use in hair cosmetics, 0.01 to 1 mol of comb-shaped hydrophobic diol is suitably used for 1 mol of polyalkylene glycol (x is 0.01 to 0.5). When the number of mol of the comb-shaped hydrophobic diol is in this range, the product has a sufficient thickening effect needed for a mortar thickening agent etc. or a sufficient hydrophobic nature needed for an underwater concrete thickening agent, a ceramics forming binder, a moisturizer for hair cosmetics and has its solubility satisfactorily maintained. The values in parenthesis indicates the value x in the above-described general formula (8).

As described above, when using polyethylene glycol with a number average molecular weight of 3,000 to 20,000 as polyalkylene glycol, the most excellent polyurethane as an extruding auxiliary, an underwater concrete thickening agent, etc. is likely to be produced. In this case, the amount of comb-shaped hydrophobic diol used in the reaction is preferably 0.01 to 1 mol for 1 mol of polyethylene glycol (x is 0.01 to 0.5), more preferably 0.03 to 0.67 mol (x is 0.03 to 0.4). When the amount of the comb-shaped hydrophobic diol is in this range, a product has a satisfactory effect as an extruding auxiliary, an underwater concrete thickening agent.

The suitable reaction temperature varies depending on the type and amount of the catalyst used; however, it is preferably in the range of 50 to 180° C., more preferably in the range of 60 to 150° C., and much more preferably in the range of 80 to 120° C. When the reaction temperature is in the range of 50 to 180° C., the reaction rate is sufficiently high, therefore, the production is economical; in addition, the product is not subjected to thermal decomposition.

The reaction time varies depending on the type and amount of the catalyst used, and it is not limited to any specific time. A product can be obtained satisfactorily when the reaction time is 1 minute to 10 hours.

The reaction pressure is not limited to any specific pressure. The reaction can be conducted at normal pressures, reduced pressures and increased pressures. The reaction is preferably conducted at normal pressures or slightly increased pressures.

The product obtained after the completion of the reaction can be subsequently subjected to grinding process, if necessary. In this case, the product obtained by the reaction is taken from the reactor and ground into particles of suitable diameter, for example, of diameter not more than 1 mm. For the grinding, apparatus commonly used for grinding polymers having a relatively low melting point, such as freeze grinder, impact grinder and grinding-type crusher.

Now the characteristics of water-soluble polyurethane obtained according to the present invention will be described below.

According to the present invention, there is obtained water-soluble polyurethane whose 2.5% aqueous solution viscosity (the viscosity of polyurethane aqueous solution whose polyurethane concentration is 2.5% by weight is measured with B type rotating viscometer at 6 rpm at 25° C.) is about 100 mPa·s to 1,000,000 mPa·s or higher.

The weight average molecular weight of the polymer obtained according to the present invention is in the range of about 10,000 to 10,000,000.

The water-soluble polyurethane can be used in the solid flake state, or in the aqueous solution or alcohol dilute solution states.

Since the water-soluble polyurethane according to the present invention is excellent in viscosity characteristics, solubility in water or in polar solvents, moisture retention, etc., it can be suitably used as an extruding auxiliary for cement materials, a mortar thickening agent, an underwater concrete thickening agent, a ceramics forming binder and a moisturizer for hair cosmetics, as described below. However, those skilled in the art will easily recognize that the present invention is not limited in its application to the above examples and it can be used in the other various applications, either, because of its characteristics.

Extruding Auxiliary

The above-described water-soluble polyurethane according to the present invention is suitably used as an extruding auxiliary for use in a cement material.

As described above, the water-soluble polyurethane according to the present invention is allowed to have a viscosity of a 2.5% aqueous solution of about 100 to 1,000,000 mPa·s; however, when using it as, in particular, an extruding auxiliary for a cement material, it has a 2.5% aqueous solution viscosity of preferably 1,000 to 1,000,000 mPa·s, and more preferably 10,000 to 500,000 mPa·s. For the water-soluble polyurethane having a 2.5% aqueous solution viscosity of about 1,000 to 1,000,000 mPa·s, when being used as an extruding auxiliary, it hardly permits water to separate from the cement material during extrusion since it has a satisfactory water retention, it imparts a moderate tackiness to the material, and it allows the surface of the extruded forms to be kept satisfactorily smooth.

When mixing 40 parts by weight of polymer aqueous solution whose polymer concentration is 2.5% and 100 parts by weight of cement, the ratio of the polymer to the cement becomes 1% by weight and the ratio of water to the cement becomes 40% by weight, and these ratios are typical for extrusion mortar, as described later. Accordingly, in order to define the characteristics of an extruding auxiliary, its 2.5% aqueous solution viscosity is suitably used.

For the polyurethane according to the present invention, its weight average molecular weight measured by the GPC is preferably in the range of 100,000 to 1,000,000 when being used as an extruding auxiliary. In the GPC, chloroform solution was used. And the molecular weight was obtained by calibrating the measurements using standard polystyrene as a standard reference material. When the polyurethane has a weight average molecular weight of in this range, it is suitable to be an extruding auxiliary, because its aqueous solution viscosity is satisfactory and its solution does not show stringiness.

When being used as an extruding auxiliary, the above polyurethane is more preferably in the powder state, in terms of handlability. The powder of particle diameter 16 mesh (1 mm) or less is preferably used. The reason is that the powder of particle diameter 16 mesh (1 mm) or less exhibits a satisfactory solubility.

One of characteristics of the present invention is that the viscidity of the new mortar which is prepared by adding the aforementioned polyurethane is lower than that of the prior-art mortar which is prepared by adding a polyurethane using the conventional hydrophobic diol, which is followed by a fact that the extrusion molding of cement is sustained at a low discharge pressure. The reason for enjoying the low viscosity has not been fully clarified yet at present; however, as a causation the structure of the primary amine would be considerable. Namely, it is presumed that the movability between the hydrocarbon group and the amino group in the amine compound is enhanced by the insertion of 1 to 16 (number of k+1) alkyleneoxy group(s) each having 2 to 10 carbon atoms, which insertion results in the introduction of ether linkage(s) into the compound, and thus, the association and dissociation between the hydrophobic groups would be caused with vigorous.

The above extruding auxiliary may contain an anti-oxidant, a stabilizer, a plasticizer, a diluent, an anti-caking agent, grinding auxiliary, etc. besides the above water-soluble polyurethane as a chief ingredient.

Extruding Composition of a Cement Material

As the extruding compositions of a cement material used in the present invention, the compositions equivalent to the known extruding compositions of a cement material are effectively used, provided that those compositions contain the extruding auxiliaries according to the present invention instead of cellulose ethers, such as methyl cellulose and hydroxypropyl methyl cellulose, which have been used as an extruding auxiliary.

Specifically, the extruding compositions of cement material used in the present invention contain hydraulic powder, such as normal portland cement, special portland cement, portland blastfurnace slag cement, portland fly-ash cement, high alumina cement and plaster, as a chief ingredient, fine aggregates, fiber, water and extruding auxiliaries.

Although extrusion can be carried out without a fine aggregate, it is usually used so as to improve the accuracy for dimensions of extruded articles and reduce the raw material costs. As a fine aggregate, sand is mostly used; however, light-weight aggregates such as pearlite, vermiculite, shirasu balloon, pumice, shattered foamed concrete and shattered foamed plastics can be used, as well.

Fibers are added so as to improve the shape retention of the compositions (mortar). As the fibers preferably used are various types of fibers such as asbestos, rock wool, glass fiber, carbon fiber and polymer fibers. In terms of safety, fibers other than asbestos (hereinafter abbreviated as asbestos-substitute fibers), such as rock wool, glass fiber, carbon fiber and polymer fiber (polypropylene fiber, Vinylon fiber, aramid fiber, etc.) are more preferably used.

The compositions may contain, for example, inorganic materials such as fly ash, silica fume, bentonite and clay; pulp; water absorbing agents such as water absorbing resin; reemulsified resin powder; various types of water reducing agents; surfactants; and anti-foaming agents.

The amount of the extruding auxiliary of the present invention added varies depending on the composition of the mortar; however, the amount is usually about 0.1 to 5% by weight per 100% by weight of hydraulic powder contained in the extruding cement compositions for building material, more preferably 0.2 to 3% by weight, and much more preferably 0.5 to 1.5% by weight. When the amount of the extruding auxiliary added is in the range of 0.1 to 5% by weight, the extruding auxiliary works effectively, the compositions develop a moderate tackiness, and satisfactory results are obtained in terms of productivity. The optimum amount varies depending on the concrete extrusion conditions such as composition of extrusion compositions, performance of extruder and shape of extruded articles; however, generally satisfactory results are obtained when adding the extruding auxiliary in an amount 50 to 95% by weight of the cellulose ethers having been added in the conventional compositions. The method of adding the extruding auxiliary may be such that the extruding auxiliary in the dried flake or dried powder state and the other ingredients of the cement compositions are mixed while stirring or such that first the aqueous solution of the extruding auxiliary is made and the solution is added to the other ingredients of the cement composition.

It goes without saying that the extrusion thickening agent of the present invention can be used as the extruding auxiliary in combination with the currently used thickening agents such as cellulose ethers, polyacrylamide polymers, polyethylene oxides and polyvinyl alcohols.

The ratio of water contained in the above composition varies depending on the type and amount of the fine aggregate and fiber used; however, the suitable weight ratio of water to hydraulic powders, such as cement, (water-cement ratio) is preferably in the range of 0.2 to 1, more preferably in the range of 0.3 to 0.7, and much more preferably 0.3 to 0.4. When the water-cement ratio is in the range of 0.2 to 1, the water content required for the hydration of the cement becomes moderate, and extruded articles of high flexural strength are obtained. In order to obtain extruded articles of high strength, the water-cement ratio is more preferably in the range of 0.3 to 0.7, and much more preferably in the range of 0.3 to 0.4. When the water-cement ratio is in the range of 0.3 to 0.4, the extruded articles of the highest strength are likely to be produced.

The amount of fine aggregate added to the compositions may be almost the same as that of the aggregate added to the conventional extrusion mortar; typically, the amount of fine aggregate, such as sand, added to the compositions is preferably about 10 to 500% by weight per 100% by weight of hydraulic powders, and more preferably 30 to 300% by weight.

The amount of fiber added to the compositions varies depending on the shape of extruded articles to be obtained; however, one of the advantages of using the extruding auxiliary of the present invention is, for example, that the addition of fiber even in an amount smaller than that of the conventional extrusion allows the mortar to have a sufficient shape retention. When using asbestos as a fiber, the amount of the asbestos used in the compositions may be decreased to about 70 to 95% of that of the conventional mortar. The use of asbestos-substitute fibers such as polymer fibers is much more effective in decreasing the amount of fiber used in the compositions. It allows the amount of fiber to be decreased to about 50 to 90% of that of the conventional mortar. The reason why the use of asbestos-substitute fibers is much more effective in decreasing the amount of fibers used in the compositions is that asbestos-substitute fibers are inferior to asbestos in shape retention. The lack of shape retention of those fibers can be supplemented with the extruding auxiliary of the present invention. Typically, the amount of fiber added to the compositions is preferably about 0.1 to 10% by weight per 100% by weight of hydraulic powders added to the same, more preferably 0.5 to 5% by weight.

These cement material compositions can be extruded in the conventional manner, that is, in such a manner that they are kneaded with a kneader and then extruded with an extruder for cement material extrusion.

The present invention is not intended to be limited to any specific kneading methods; however, in the production of extrusion mortar, the kneading is generally carried out in such a manner that an required amount of each ingredient, such as cement, fine aggregate, extruding auxiliary and fiber, is introduced from each hopper into a mixer and fully mixed, after that, a required amount of water is added to and mixed with the mixture, then the mixture is transferred to a kneader, etc., so as to be kneaded.

The kneaded composition is extruded with, for example, a vacuum extruder into various extruded articles such as cement plate, hollow cement plate, cement siding board, column and pipe. These extruded articles are subjected to steam curing or autoclave curing so as to be completed products.

Mortar Thickening Agent

The above-described water-soluble polyurethane according to the present invention is suitably used as a thickening agent for a mortar (a mortar thickening agent).

As a mortar thickening agent, desirably used is the polyurethane in which the molar ratio of the repeating unit (U-1) represented by the aforementioned general formula (3) is 0.5 or more and 0.99 or less and the molar ratio of the repeating unit (U-2) represented by the aforementioned general formula (4) is 0.01 or more and 0.5 or less, and whose 2% aqueous solution viscosity at 20° C. is in the range of 10 mPa·s to 300,000 mPa·s.

When polyurethane has a 2% aqueous solution viscosity within this range, it acts on mortar sufficiently as a thickening agent, in addition, its action as a polymer thickening agent is moderate, therefore, the workability of mortar is improved. The polymer having a 2% aqueous solution viscosity at 20° C. is more preferably in the range of 50 to 100,000 mPa·s. The 2% aqueous solution of the polymer is obtained by dissolving 2 g of the polymer in 98 g of distilled water.

For measuring an aqueous solution viscosity, a rotating cylinder viscometer widely use is used. The measurement is carried out using a 2% aqueous solution whose temperature is controlled at 20° C. and at a rotating speed of the cylinder of the viscometer of 6 rpm. However, in cases where the sample has a aqueous solution viscosity exceeding 100,000 mPa·s, the measurement is carried out at a rotating speed of 4 rpm.

For the mortar thickening agents according to the present invention, preferably most of the particles constituting the water-soluble polyurethane powder used have a diameter 1 mm or less. More preferably 95% by weight or more of the particles have a diameter 1 mm or less and 50% by weight or more of the particles have a diameter 600 $\mu$m or less. Much more preferably 99% by weight or more of the particles have a diameter 1 mm or less and 50% by weight or more of the particles have a diameter 400 $\mu$m or less. When the percentage of the particles having a diameter more than 1 mm is low, the solubility of the water-soluble polyurethane is improved.

The mortar thickening agents may have additives, such as anti-oxidant, stabilizer, plasticizer, dilluent, anti-caking agent and grinding auxiliary, added thereto.

The thickening agents of the present invention are characterized, for example, in that although they cause less retardation of setting than the thickening agents comprising cellulose ethers, they have thickening effects equivalent to the thickening agents comprising cellulose ethers.

The reasons that the thickening agents of the present invention have such excellent characteristics have not been fully clarified yet at present; however, the following discussion may be drawn.

Presumably, the mechanism of cellulose ethers' thickening action in mortar is such that hydrophobic groups such as methyl groups, which are substituents for hydroxyl groups of cellulose units, interact with each other in a hydrophobic manner and polymer chains form an associated molecule via the hydrophobic groups.

On the other hand, the polymers used in the present invention have comb-shaped hydrophobic groups (a kind of aggregate of hydrophobic groups), which originate from comb-shaped hydrophobic diols as a raw material, in their chains and they can form an associated molecule effectively even with a small number of hydrophobic groups. The phenomenon is described in detail in Japanese Patent Laid-Open No. 59-78226 that polymers having aggregates of several hydrophobic groups form a network structure when the aggregates of hydrophobic groups associate with each other, as a result of which the viscosity of the polymer aqueous solution is enhanced.

The mechanism of cellulose ethers' retarding setting of mortar has not been fully clarified yet at present; however, it is presumed that (a) hydroxyl groups of cellulose units bond to calcium in mortar, which retards the hydration reaction of cement and (b) cellulose ethers are adsorbed on cement particles by hydrophobic groups such as methyl group, which retards the hydration reaction of cement.

On the other hand, the polymers used in the present invention have no hydroxyl groups in their repeating units; accordingly, there are unlikely to occur bonding between hydroxyl groups and calcium. In addition, the polymers have only a small number of hydrophobic groups in their chains; therefore, their amount adsorbed on cement particles is small, which causes less retardation of mortar setting than in cases where cellulose ethers are used.

Now the differences between the polymers having hydrophobic aggregates, which are disclosed in Japanese Patent Laid-Open No. 59-78226, (hereinafter referred to as polymers of the literature cited) and the polymers used in the present invention will be described below.

The literature cited discloses that diols having hydrophobic aggregates are obtained by subjecting several molecules of the compounds containing oxirane, such as 1,2-epoxyalkanes, to addition to low-molecular weight diols, such as diethylene glycol, (hereinafter referred to as spacer) using an acid or alkaline catalyst. And alternatively, it discloses that diisocyanates and diols having hydrophobic aggregates are obtained by reacting diols, which are obtained by subjecting 2 molecules of glycidyl ethers to addition to methylamine, with diisocianates.

With these methods, however, hydrophobic aggregates of a fixed number of hydrophobic groups cannot be obtained, and in actuality, obtained was only the mixture of several kinds of hydrophobic aggregates different in the number of hydrophobic groups. This is attributed to the fact that hydroxyl groups produced by the reaction of glycols of the spacer with the compounds containing oxirane further react with the compounds containing oxirane; therefore, various diols are produced which differ in the number of compounds containing oxirane added to the spacer. When bonding diols with diisocyanates, the mixture of several kinds of diisocyanates and diols different in the number of hydrophobic groups is produced.

Thus, it is considered that the polymers of the literature cited are those having a plurality of hydrophobic aggregates different in the number of hydrophobic groups in their molecules.

For the thickening agents using polymers having a plurality of hydrophobic aggregates, which are different in the number of hydrophobic groups, in their molecules, their solubility in mortar is likely to deteriorate and they are likely to cause retardation of mortar setting. Since the number of the hydrophobic groups of each hydrophobic aggregate has distribution, it is unavoidable that the polymers contain hydrophobic aggregates having a large number of hydrophobic groups, and hence, having an unnecessarily strong hydrophobic nature in a certain ratio. Presumably, these hydrophobic aggregates having too strong hydrophobic nature cause the deterioration of solubility of thickening agents and retardation of mortar setting.

On the other hand, the polymers of the present invention are characterized in that they contain hydrophobic aggregates having substantially same number of hydrophobic groups; thus, they can prevent bad effects due to the existence of hydrophobic aggregates having too strong hydrophobic nature.

As described above, the mortar thickening agents of the present invention decrease retardation of setting, which is one of the disadvantages of the currently used thickening agents, while having a thickening effect equivalent to that of the currently used thickening agents. Thus, they are available for a wide range of applications such as tile-bonding mortar, masonry mortar, spraying mortar, repairing mortar, substrate mortar and topping mortar and can contribute greatly to making building construction and public works construction more efficient and more reliable, and reducing the costs thereof.

Mortar Composition

Now the application of the thickening agents comprising the above polymer to mortar thickening agent will be described.

Dry mortar compositions can be obtained by formulating (1) hydraulic inorganic powders such as portland cement, alumina cement and calcium silicate, (2) fine aggregates such as sand, fly ash, silica fume, pearlite, pumice, shattered foamed concrete and shattered foamed plastics and hollow polystyrene particles, and (3) the thickening agents according to the present invention and fully mixing the same. However, the fine aggregates (2) are not always necessary.

In addition to the above ingredients, the other currently used ingredients for the preparation of mortar can be added, according to the need. For example, various types of water reducing agent, reemulsified resin powder, anti-foaming agent and fiber. When these ingredients are powder (solid), these are mixed with the above ingredients (1), (2) and (3), so as to obtain dry mortar.

Suitably, 0.01 to 5% by weight of the thickening agent is added per 100% by weight of all the dry mortar, more preferably 0.1 to 1% by weight.

When the amount of the thickening agent added is in the range of 0.01 to 5% by weight, the effects of thickening agent is developed satisfactorily; in addition, since the amount is a necessary and sufficient amount for obtaining the desired effects of the thickening agent, it is preferable from the economical viewpoint.

The amount of the hydraulic inorganic powder added varies depending on the application of mortar and the amount of the fine aggregate used; however, preferably about 99.99 to 10% by weight is added per 100% by weight of all the dry mortar, preferably 80 to 20% by weight.

The amount of the fine aggregate added varies depending on the application of mortar and the type of the fine aggregate used; however, preferably about 89.99 to 0% by weight is added per 100% by weight of all the dry mortar, preferably 80 to 20% by weight.

When adding water to this dry mortar in such an amount as satisfies the required water-cement ratio (the weight ratio of water to hydraulic inorganic powder) and then fully kneading the mixture, mortar can be obtained.

A suitable water-cement ratio is about 0.2 to 1, more preferably 0.3 to 0.7.

When the water-cement ratio is in the range of 0.2 to 1, the amount of water required for the hydration reaction of cement is ensured, and the strength of mortar after curing becomes satisfactory.

Underwater Concrete Thickening Agent

The above-described water-soluble polyurethane according to the present invention is suitably used as an thickening agent for an underwater concrete.

As an underwater concrete thickening agent, desirably used is the water-soluble polyurethane according to the present invention in which the molar ratio of the repeating unit (U-1) represented by the aforementioned general formula (3) is 0.5 or more and 0.99 or less and the molar ratio of the repeating unit (U-2) represented by the aforementioned general formula (4) is 0.01 or more and 0.5 or less, and preferably the polymer has the weight average molecular weight, which is measured by GPC, in the range of 100,000 to 1,000,000.

In the GPC, chloroform solution was used. And the molecular weight was obtained by calibrating the measurements using standard polystyrene as a standard reference material. When the polyurethane has a weight average molecular weight in the range of 100,000 to 1,000,000, it is suitable to be an underwater concrete thickening agent, because its aqueous solution viscosity is satisfactory and its solution does not show stringiness.

As an underwater concrete thickening agent of the present invention, effectively used is the polyurethane whose 2% aqueous solution viscosity (viscosity of aqueous solution whose polyurethane content is 2% by weight at 20° C. measured with a B type rotating viscometer at 6 rpm) is in the range of about 1,000 to about 500,000 mPa·s, more preferably in the range of 10,000 to 300,000 mPa·s. When polyurethane has a 2% aqueous solution viscosity in the range of about 1,000 to about 500,000 mPa·s, the anti-aggregate-separating properties of concrete is satisfactory, in addition, the tackiness of the same is moderate, therefore, a satisfactory pumpability of concrete is obtained.

When being used as an underwater concrete thickening agent, the above polyurethane may be in the solid flake state and in the distilled aqueous or alcohol solution state; however, more preferably it is in the powder state, in terms of handlability. The powder of particle diameter 16 mesh (1 mm) or less is preferably used. The reason is that the powder of particle diameter 16 mesh (1 mm) or less exhibits a satisfactory solubility.

The above underwater concrete thickening agent may contain an anti-oxidant, a stabilizer, a plasticizer, a diluent, an anti-caking agent, grinding auxiliary, etc. besides the above water-soluble polyurethane as a chief ingredient.

Underwater Concrete Composition

As the compositions for an underwater concrete (an underwater concrete composition) used in the present invention, the compositions equivalent to the known underwater concrete compositions are effectively used, provided that those compositions contain the underwater concrete thickening agents according to the present invention instead of cellulose ethers, such as methyl cellulose and hydroxypropyl methyl cellulose, which have been used as an underwater concrete thickening agent. Specifically, the underwater concrete compositions used in the present invention contain hydraulic powder, such as normal portland cement, special portland cement, portland blastfurnace slag cement, portland fly-ash cement, high alumina cement and plaster, as a chief ingredient, fine aggregates, coarse aggregates and water in addition to the above underwater concrete thickening agent of the present invention.

The compositions may contain, for example, inorganic materials such as fly ash, silica fume, bentonite and clay; reemulsified resin powder; various types of water reducing agents; surfactants; anti-foaming agents, accelerating agents and retarding agents.

The amount of the underwater concrete thickening agent of the present invention added varies depending on the composition of the concrete used; however, the amount is usually about 0.1 to 10% by weight per 100% by weight of hydraulic powder such as cement, more preferably 0.2 to 5% by weight, and much more preferably 0.5 to 5% by weight. When the amount of the underwater concrete thickening agent added is in the range of 0.1 to 10% by weight, the underwater concrete thickening agent works effectively, and it imparts moderate tackiness and it does not allow the workability to deteriorate.

One of the characteristics of the underwater concrete thickening agents of the present invention is that, when being added to cement in the ratio of 10% by weight, they hardly cause retardation of concrete setting. For the currently used thickening agents such as cellulose ethers, however, even when 0.5 to 5% by weight of thickening agents are added per 100% by weight of cement, they are likely to cause retardation of concrete setting, and hence, deterioration of concrete strength.

The method of adding the thickening agents to the concrete may be such that the thickening agents in the powder state are added to and dissolved in concrete while stirring or such that an aqueous solution of the thickening agents is added to concrete or such that the mixture of the underwater concrete thickening agents and cement previously prepared is used as a raw material of concrete.

It goes without saying that the underwater concrete thickening agent of the present invention can be used in combination with the currently used thickening agents such as cellulose ethers, polyacryl polymers, polyethylene oxides and polyvinyl alcohols.

The ratio of water contained in the above composition varies depending on the type and amount of the fine aggregate and coarse aggregate used; however, the suitable weight ratio of water to hydraulic powders, such as cement, (water/cement ratio) is preferably in the range of 0.2 to 1, more preferably in the range of 0.3 to 0.7, and much more preferably 0.3 to 0.5. When the water/cement ratio is in the range of 0.2 to 1, the water content required for the hydration of the cement is moderately ensured, and concrete of satisfactory strength is obtained.

The amount of fine aggregates added may be almost the same as that of the aggregates added to the conventional underwater concrete; typically, the amount of fine aggregates, such as sand, added is about 10 to 500% by weight per 100% by weight of hydraulic powders, such as cement.

The amount of coarse aggregates added may be almost the same as that of the coarse aggregates added to the conventional underwater concrete; typically, the amount is about 10 to 500% by weight per 100% by weight of hydraulic powders, such as cement.

Although the present invention is not limited to any specific underwater concrete production methods, the underwater concrete of the present invention can be produced, for example, in such a manner that a predetermined amount of powder of the underwater concrete thickening agents or its aqueous solution is added to and mixed with ready-mixed concrete. Alternatively, the mixture of cement and the powder of the underwater concrete thickening agent previously prepared can be used as a raw material of concrete.

The underwater concrete compositions thus obtained can be placed in the same manner as the currently used concrete. For example, the compositions is supplied underwater by allowing them to freely fall underwater or using a transport pump, or via a bucket, chute, hose or Lamy pipe, then cured underwater.

Ceramics Forming Binder

The above-described water-soluble polyurethanes according to the present invention are suitably used as a ceramics forming binder.

As a ceramics forming binder, preferably used are the polyurethanes in which the molar ratio of the repeating unit (U-1) represented by the aforementioned general formula (3) is 0.5 or more and 0.99 or less and the molar ratio of the repeating unit (U-2) represented by the aforementioned general formula (4) is 0.01 or more and 0.5 or less, and the polymers preferably have the weight average molecular weight, as measured by GPC, in the range of 10,000 to 1,000,000, more preferably in the range of 10,000 to 500,000.

In GPC, chloroform solution was used. And the molecular weight was obtained by calibrating the measurements using standard polystyrene as a standard reference material. When the polyurethanes have a weight average molecular weight in the range of 10,000 to 1,000,000, they are suitable to be a binder, because their plasticity and caking are satisfactory.

The ceramics forming binders comprising these polyurethanes are easily dissolved in water and in polar organic solvents such as ethanol.

When using these soluble polyurethanes as a ceramics forming binder, other ingredients, which have been used in ceramics forming, may be added to the polyurethanes according to the purpose, so as to obtain ceramics forming compositions. These ingredients include, for example, various types of surfactants, propylene glycol, liquid paraffin, glycerol, ethanolamine, wax emulsion, stearic acid and the salts thereof, alcohols and anti-foaming agents.

The amount of the ceramics forming binder of the present invention varies depending on the type of the ceramic product to be obtained; however, the amount is, for example, preferably about 0.1 to 10% by weight per 100% by weight of ceramics, more preferably 0.5 to 5% by weight.

The present invention is not intended to be limited to any specific ceramics; however, ceramics applicable to the binders of the present invention include not only alumina, but also barium titanate, zirconia, silicon carbide, silicon nitride and other fine ceramics in general.

The ceramics forming binders of the present invention are preferably used as a ceramics extrusion binder. And there are many forming methods to which the binders of the present invention are applicable. Specifically, they are applicable not only to the extrusion process, but also to sheet forming, tape forming and pressing. Since they are thermoplastic resins, they can be used in injection molding. In any cases, they are superior to the currently used binders particularly in their moderate heat release during calcination.

The reasons have not been fully clarified yet that the heat release of the binders of the present invention during combustion is very moderate and the carbon residue content is low; however, presumably, the reasons are that urethane bond is susceptible to thermal decomposition, the elemental structures of the polymers contain a large number of oxygen, therefore, the heat generated due to oxidation is small, and that the molecules do not have a ring structure susceptible to carbonization.

Moisturizer for Hair Cosmetics

The above-described water-soluble polyurethanes according to the present invention are suitably used as a moisturizer for hair cosmetics. The moisturizers according to the present invention, which use these polyurethanes, impart to hair excellent characteristics such as soft feel and neither oily nor dry feel.

As a moisturizer for hair dressing, desirably used are the polyurethanes in which the molar ratio of the repeating unit (U-1) represented by the aforementioned general formula (3) is 0.5 or more and 0.99 or less and the molar ratio of the repeating unit (U-2) represented by the aforementioned general formula (4) is 0.01 or more and 0.5 or less, and the polymers preferably have the weight average molecular weight, which is measured by GPC, in the range of 10,000 to 1,000,000, more preferably 10,000 to 500,000.

In GPC, chloroform solution was used. And the molecular weight was obtained by calibrating the measurements using standard polystyrene as a standard reference material. When the polyurethanes have a weight average molecular weight in the range of 10,000 to 1,000,000, they are suitable to be moisturizers for use in hair cosmetics, because they impart satisfactory water retention to hair cosmetics and the hair cosmetics impart to hair moderate feel, neither oily nor dry feel.

The moisturizers for hair cosmetics comprising these polyurethanes are easily dissolved in water and in polar organic solvents such as ethanol.

When preparing hair cosmetics using these moisturizers comprising soluble polyurethanes, other ingredients, which have been used in hair cosmetics field, may be added according to the purpose, so as to prepare hair cosmetics compositions. These ingredients include, for example, various types of surfactants, propylene glycol, liquid paraffin, glycerol, silicone oil, ethanol, sequestering agents such as EDTA, perfume, preservatives and purified water.

Industrial Field of the Invention

As describe above, according to the present invention, polyurethanes having improved characteristics such as viscosity characteristics, solubility and moisture retention can be obtained.

As a result, extruding auxiliaries are available which have high shape retention as well as improved viscidity, and what is more, are inexpensive. Further, with these extruding auxiliary, the shape retention of mortar using asbestos-substitute fibers can be improved. And moreover, extruded cement plates having improved strength can be obtained.

Further, mortar thickening agents can be obtained which have thickening effects equivalent to those of the currently used thickening agents, though they cause less retardation of setting, and which can impart to mortar thixtropic properties as well as water retention necessary and sufficient for placing of mortar. Thus, in building construction and public works construction, these mortar thickening agents can contribute largely to making their processes more efficient, improving their reliability and reducing their costs.

Still further, according to the present invention, underwater concrete thickening agents are available which can impart high underwater anti-separating properties as well as improved strength to underwater concrete, and what is more, are inexpensive.

Further, according to the present invention, ceramics forming binders having a high productivity are available.

Still further, according to the present invention, moisturizers for use in hair cosmetics are available which have high moisture retention and can impart moist feel to hair.

EXAMPLES

The present invention will be described with reference to the following examples; however, it is to be understood that these examples are shown for illustrative purposes only and are not intended to limit the present invention.

(Syntheses Examples of Comb-shaped Hydrophobic Diol)

Example 1

A 500 ml round flask was equipped with a magnetic stirrer, a thermometer and a dropping funnel, 93.6 g of 3-[(2-ethylhexyl)oxy]-1-propylamine (manufactured by Koei Chemical Co., Ltd.) was added into the flask, and the interior atomosphere of the flask was replaced with nitrogen. The flask was heated to 60° C. in an oil bath, and then 188.0 g of 2-ethylhexylglycidyl ether (manufactured by Nagase Chemical Industry Co., Ltd. Denacol EX-121, epoxy number 188) was added dropwisely to the flask from the dropping funnel over 40 minutes while stirring the contents of the flask. After completion of the dropping, the temperature of the oil bath was raised to 80° C. and the flask was heated for 10 hours. Then the temperature of the oil bath was further raised to 120° C., a small amount of unreacted substance was distilled off under reduced pressure with a vacuum pump at a vacuum degree of 3 mmHg. Comb-shaped hydrophobic diol 1 (average molecular weight obtained from OH number was 560) in which 2-ethylhexylglycidyl ether was subjected to addition to 3-[(2-ethylhexyl)oxy]-1-propylamine in the ratio of 2:1 mol was obtained in a yield of 98%.

Example 2

Comb-shaped hydrophobic diol 2 was synthesized from 3-(butyloxy)-1-propylamine (manufactured by Tokyo Chemical Industry Co., Ltd.) and n-butylglycidyl ether (manufactured by Tokyo Chemical Industry Co., Ltd.).

Example 3

Comb-shaped hydrophobic diol 3 was synthesized from 3-(butyloxy)-1-propylamine (manufactured by Tokyo Chemical Industry Co., Ltd.) and 2-ethylhexylglycidyl ether.

Example 4

Comb-shaped hydrophobic diol 4 was synthesized from 3-(dodecyloxy)-1-propylamine (manufactured by Koei Chemical Co., Ltd.) and 2-ethylhexylglycidyl ether.

Example 5

Comb-shaped hydrophobic diol 5 was synthesized from 3-(dodecyloxy)-1-propylamine (manufactured by Koei Chemical Co., Ltd.) and dodecylglycidyl ether (obtained by subjecting dodecyl/tetradecylglycidyl ether manufactured by Ardrich to distillation purification).

Example 6

Comb-shaped hydrophobic diol 6 was synthesized from 2-ethoxyethylamine (manufactured by Tokyo Chemical Industry Co., Ltd.) and n-octyl glycidyl ether (manufactured by P & B).

Example 7

Comb-shaped hydrophobic diol 7 was synthesized from 4-methoxybutylamine (Sigma—Ardrich Japan Co., Ltd.) and octadecyl glycidyl ether (Nippon Oil and Fats Co., Ltd., Epiol SK).

Example 8

Comb-shaped hydrophobic diol 8 was synthesized from 3-(butyloxy)-1-propylamine (manufactured by Tokyo Chemical Industry Co., Ltd.) and octadecyl glycidyl ether (Nippon Oil and Fats Co., Ltd., Epiol SK).

These results are shown in Table 1.

Table 1

Examples of Comb-shaped Hydrophobic Diol Syntheses
Structural Formula of Compounds:

$R^2$—$OCH_2CH(OH)CH_2N(R^1)CH_2CH(OH)CH_2O$—$R^3$

| Example No. | $R^1$ | $R^2$, $R^3$ | Molecular Weight obtained from OH Number |
|---|---|---|---|
| Example 1 | —$(CH_2)_3OCH_2CH(CH_2)_3CH_3$ / —$CH_2CH_3$ | —$CH_2CH(CH_2)_3CH_3$ / —$CH_2CH_3$ | 560 |
| Example 2 | —$(CH_2)_3O(CH_2)_3CH_3$ | —$(CH_2)_3CH_3$ | 390 |
| Example 3 | —$(CH_2)_3O(CH_2)_3CH_3$ | —$CH_2CH(CH_2)_3CH_3CH_2CH_3$ | 507 |
| Example 4 | —$(CH_2)_3O(CH_2)_{11}CH_3$ | —$CH_2CH(CH_2)_3CH_3$ / —$CH_2CH_3$ | 620 |
| Example 5 | —$(CH_2)_3O(CH_2)_{11}CH_3$ | —$(CH_2)_{11}CH_3$ | 695 |
| Example 6 | —$(CH_2)_2OCH_2CH_3$ | —$(CH_2)_7CH_3$ | 460 |
| Example 7 | —$(CH_2)_4OCH_3$ | —$(CH_2)_{17}CH_3$ | 754 |
| Example 8 | —$(CH_2)_3O(CH_2)_3CH_3$ | —$(CH_2)_{17}CH_3$ | 780 |
| Comparative Example 1 | —$CH_2CH(CH_2)_3CH_3$ / —$CH_2CH_3$ | —$CH_2CH(CH_2)_3CH_3$ / —$CH_2CH_3$ | 490 |

Comparative Example 1

Hydrophobic diol different in type from those of the present invention was synthesized from 64.6 g of 2-ethylhexylamine (manufactured by Kanto Chemical Co., Ltd.) and 188 g of 2-ethylhexylglycidyl ether. The average molecular weight was 490.

(Examples of Water-soluble Polyurethane Syntheses)

Examples of syntheses of water-soluble polyurethane using the hydrophobic diols of the examples will be described below; however, it should be understood that these examples are shown for illustrative purposes only and are not intended to limit the present invention.

Example 9

100 g of commercially available polyethylene glycol (PEG#6000, manufactured by Genuine Chemical Co., Ltd., number average molecular weight 8,700) was added into a 500 ml separable flask made of SUS and was allowed to melt under nitrogen seal at 150° C. This molten PEG was subjected to drying under reduced pressure (3 mmHg) for 3 hours while stirring. The residual water content was 200 ppm. The temperature of the flask was reduced to 80° C., and 0.80 g of the comb-shaped hydrophobic diol 1 obtained in the example 1 and 2.30 g of hexamethylene diisocyanate (HDI) (manufactured by Tokyo Chemical Industry Co, Ltd.,) were added into the flask while stirring the contents of flask. When adding 0.01 g of dibutyltin dilaurate (DBTDL) as a catalyst, the contents of the flask became viscous rapidly after about 10 minutes. Then the stirring was stopped, and the reaction was allowed to progress for another two hours.

After completion of the reaction, the product was taken out from the flask, cut into small pieces and allowed to stand to be cooled. The cooled product was further cooled with liquid nitrogen and pulverized into particles of diameter 1 mm (16 mesh) or smaller with an electric mill.

The 2.5% aqueous solution viscosity of the product was determined as 100,000 mPa·s and the weight average molecular weight measured by the GPC was 480,000.

Now the method of measuring 2.5% aqueous solution viscosity will be explained. 2.5 g of polymer was dissolved in 97.5 g of distilled water so as to obtain 2.5% aqueous solution. This aqueous solution was added into a beaker, the beaker was dipped in a constant emperature bath kept at 25° C., and the viscosity of the queous solution was measured with a rotating cylinder viscometer (BL type viscometer manufactured by TOKIMEC) at a rotary speed of rotor of 6 rpm. For the specimens of which aqueous solution viscosity exceeds 100,000 mPa·s, the viscosity was measured with a BH type viscometer manufactured by TOKIMEC at a rotary speed of rotor of 4 rpm.

Examples 10 to 14

Water-soluble polyurethanes were synthesized in the same manner as in the example 9, except that the amount of each of the comb-shaped hydrophobic diol 1 and HDI added into the flask was different. The amount of HDI was set so that the number of mol of HDI would become 1.03 times as large as the total number of mol of PEG and the comb-shaped hydrophobic diol (NCO/OH=1.03).

Examples 15 to 17

Water-soluble polyurethanes were synthesized in the same manner as in the examples 9 to 14, except that the molecular weight of PEGs used were in the range of 20,000 to 3,000.

Comparative Example 2

Polyurethane was synthesized using the diol synthesized in the comparative example 1. NCO/OH was 1.03. The results are shown in Table 2 together with those of the examples 9 to 17.

TABLE 2

Examples of Water-soluble Polyurethane Syntheses

| Example No. | Molecular Weight of PEG | Type of Hydrophobic Diol | Total Number of Carbon Atoms of Hydrophobic Groups | Hydrophobic Diol/PEG (%) | Coefficient of Repeating Unit X | 2.5% Aqueous Solution Viscosity (mPa · s) | Weight Average Molecular Weight (× $10^4$) |
|---|---|---|---|---|---|---|---|
| Example 9 | 8,700 | Example 1 | 24 | 0.80 | 0.11 | 100,000 | 48 |
| Example 10 | 8,700 | Example 2 | 12 | 1.0 | 0.18 | 10,000 | 38 |
| Example 11 | 8,700 | Example 3 | 20 | 0.65 | 0.10 | 1,000 | 49 |
| Example 12 | 8,700 | Example 4 | 28 | 0.40 | 0.05 | 100,000 | 47 |
| Example 13 | 8,700 | Example 5 | 36 | 0.30 | 0.04 | 300,000 | 51 |
| Example 14 | 8,700 | Example 6 | 18 | 0.80 | 0.11 | 90,000 | 46 |
| Example 15 | 20,000 | Example 7 | 37 | 0.6 | 0.06 | 1,000,000 | 100 |
| Example 16 | 3,000 | Example 8 | 40 | 0.2 | 0.01 | 2,000 | 10 |
| Example 17 | 20,000 | Example 2 | 12 | 2.0 | 0.50 | 500,000 | 90 |
| Comparative Example 2 | 8,700 | Comparative Example 1 | 24 | 0.73 | 0.11 | 100,000 | 50 |

(Syntheses Examples of Water-soluble Polyurethane for use in Mortar Thickening Agent)

In the following the syntheses examples of water-soluble polyurethane using hydrophobic diol of the example 4 will be described.

Example 18

200 g of commercially available polyethylene glycol (PEG#6000, manufactured by Sanyo Chemical Industries, Ltd., number average molecular weight 8,630) was added into a 1000 ml separable flask made of SUS and was allowed to melt under nitrogen seal at 150° C. This molten PEG was subjected to drying under reduced pressure (3 mmHg) for 3 hours while stirring. The residual water content was 200 ppm. The temperature of the flask was reduced to 70° C., and the interior atomosphere of the flask was fulfilled with 1 atom of nitrogen. 300 ppm of BHT (di-tert-butyl hydroxy toluene) was added as an anti-oxidant. 1.208 g of the comb-shaped hydrophobic diol 4 obtained in the example 4 and 3.995 g of hexamethylene diisocyanate (Tokyo Chemical Industry Co., Ltd.) (NCO/OH=0.995 mol/mol) were added into the flask while stirring contents of the flask. When adding 0.05 g of DBTDL as a catalyst, the content of the flask became viscous rapidly after about 10 minutes. Then the stirring was stopped, and the reaction was allowed to progress for another two hours at 70° C. The temperature of the flask was raised to 120° C. and kept the same for 30 minutes, then the product was taken out from the flask. The melting point of the product was about 60° C.

The product taken out from the flask was cut into small pieces and allowed to stand to be cooled. The cooled product was further cooled with liquid nitrogen and pulverized with an electric mill. The pulverized product was sieved, so as to obtain powder of diameter 600 μm or smaller as a mortar thickening agent. The average particle diameter of the powder was 400 μm. The 2% aqueous solution viscosity of the product was 67,000 mPa·s.

Now the method of measuring 2% aqueous solution viscosity will be explained. 2 g of polymer was dissolved in 98 g of distilled water so as to obtain 2% aqueous solution. This aqueous solution was added into a beaker, the beaker was dipped in a constant temperature bath kept at 20° C., and the viscosity of the aqueous solution was measured with a rotating cylinder viscometer (BL type viscometer manufactured by TOKIMEC) at a rotary speed of rotor of 6 rpm. For the specimens of which aqueous solution viscosity exceeds 100,000 mPa·s, the viscosity was measured with a BH type viscometer manufactured by TOKIMEC at a rotary speed of rotor of 4 rpm.

Examples 19 to 27

Polymers were synthesized in the same manner as in the example 18, except that the amount of each of the comb-shaped hydrophobic diol 4 and hexamethylene diisocyanate used were different. The 2% aqueous solution viscosity of the polymer obtained was measured in the same manner as in the example 18.

The formulation of each example and 2% aqueous solution viscosity of the polymer obtained are shown in Table 3.

TABLE 3

| Example No. | Hydrophobic Diol 4/PEG (wt %/PEG) | NCO/OH (mol/mol) | 2% Aqueous Solution Viscosity (mPa · s) |
| --- | --- | --- | --- |
| Example 18 | 0.60 | 0.995 | 67,000 |
| Example 19 | 0.80 | 0.995 | 300,000 |
| Example 20 | 0.50 | 0.995 | 110,000 |
| Example 21 | 0.70 | 0.970 | 110,000 |
| Example 22 | 0.90 | 0.970 | 180,000 |
| Example 23 | 0.90 | 0.960 | 150,000 |
| Example 24 | 0.50 | 0.958 | 20,000 |
| Example 25 | 0.40 | 0.951 | 170 |
| Example 26 | 0.30 | 0.950 | 60 |
| Example 27 | 0.10 | 0.950 | 14 |

Comparative Example 3

A mortar thickening agent was produced using the comb-shaped hydrophobic diol of the comparative example 1.

200 g of commercially available PEG#6000 (manufactured by Sanyo Chemical Industries, Ltd., number average molecular weight 8,630) was added into a 1000 ml separable flask made of SUS and was allowed to melt under 10 nitrogen seal at 150° C. This molten PEG was subjected to drying under reduced pressure (3 mmHg) for 3 hours while stirring. The residual water content was 200 ppm. The temperature of the flask was reduced to 70° C., and the interior atomosphere of the flask was fulfilled with 1 atom of nitrogen. 300 ppm of BHT (di-tert-butylhydroxy toluene) was added as an anti-oxidant. 1.70 g of the comb-shaped hydrophobic diol obtained in the comparative example 1 and 4.35 g of hexamethylene diisocyanate (Tokyo Chemical Industry Co., Ltd.) (NCO/OH=0.98 mol/mol) were added into the flask while stirring contents of the flask. When adding 0.05 g of DBTDL as a catalyst, the contents of the flask became viscous rapidly after about 10 minutes. Then the stirring was stopped, and the reaction was allowed to progress for another two hours at 70° C. The temperature of the flask was raised to 120° C. and kept the same for 30 minutes, then the product was taken out from the flask. The melting point of the product was about 60° C.

The product taken out from the flask was frozen and pulverized into powder of average particle diameter 400 μm. The 2% aqueous solution viscosity of the obtained polymer, which was measured in the same manner as in the example 18, was determined as 15,000 mPa·s.

(Examples of Producing Cement Extruded Articles Using Extruding Auxiliaries)

In the following, examples of producing cement extruded articles using the water-soluble polyurethane ccording to the present invention as an extruding auxiliary and the characteristics of the cement extruded articles thus produced will be described; however, it should be understood that these examples are shown for illustrative purposes only and are not intended to limit the present invention.

Examples 28 to 29 and Comparative Examples 4 to 5

Extrusion tests were conducted on plate-shaped extruded articles (cement boards) using mortar consisting of cement, sand, an asbestos-substitute fiber, extruding auxiliaries and water. Four different types of mortar were prepared having different types of extruding auxiliaries which are almost the same in 2.5% aqueous solution viscosity: water-soluble polyurethanes of the examples 9 and 12, water-soluble polyurethane of the comparative example 2, and Metholose 90SH-30000 (manufactured by Shin-Etsu Chemical Co., Ltd.), which is commercially available and widely used, added thereto in the same amount, and their discharging pressure in dies, the presence of water separation during extrusion, their surface topology, the shape retention of their extruded articles and their flexural strength after curing were compared.

100 parts by weight of ordinary portland cement, 100 parts by weight of standard sand, 1.5 parts by weight of vinylon fiber (Unitika, Vinylon Type AB Semihard) and a predetermined amount of extruding auxiliary were mixed with a high-speed mixer (Miyazaki Iron Works Co., Ltd., MHS-100) for 3 minutes. Then, water was added to this composition so that the composition had a predetermined water/cement ratio, the mixture was mixed for another 3 minutes, so as to obtain an extruding composition of cement-based material. The mortar thus obtained was kneaded with a screw-type kneader (Miyazaki Iron Works Co., Ltd., MP-30-1). The kneaded material was extruded with a screw-type vacuum extruding machine (Miyazaki Iron Works Co., Ltd., FM-30-1) at a fixed extrusion speed into plate-shaped articles 10 mm thick and 20 mm wide. The extruded articles were subjected to underwater curing for 28 days, after that, their flexural strength was measured.

Table 4 shows the type of extruding auxiliary used in each example and comparative example, the amount of the extruding auxiliary added (% by weight per 100% by weight of cement), the water/cement (W/C) ratio contained in the mortar, the discharging pressure of the mortar, the presence of water separation during the extrusion, the surface topology, the shape retention of the extruded articles and the flexural strength after curing.

Whether water separation was present or not was judged by observing the water flow from the dies during the extrusion. When no water separation was observed, the condition was judged to be good (⊚). When a little water separation was observed, but extrusion could be carried out, the condition was judged to be fair (○). And when water separation was clearly observed and extrusion could not be carried out, the condition was judged to be failure (x).

For the judgment of the surface topology, when the surface of the extruded article was smooth immediately after extrusion, the condition was judged to be good (⊚) When a little irregularity was observed, the condition was judged to be fair (○). And when irregularity was clearly observed, the condition was judges to be failure (x).

The shape retention of each extruded article was judged in such a manner that, first the extruded article immediately after extrusion was cut into pieces 20 cm long, each of the pieces were placed across the two blocks spaced at intervals of 10 cm and left stand at temperature of 25° C. and humidity of 100% for 24 hours, and finally the distance of the sag in the middle portion of the extruded article was measured. When the sag was less than 15 mm, the condition was judged to be good (⊚). When the sag was 15 mm or longer and less than 20 mm, the condition was judged to be fair (○). And when the sag was more than 20 mm, the condition was judges to be failure (x).

The flexural strength was measured in accordance with JIS R-5201.

For the mortar of the examples 28 and 29, their discharging pressure was lower than that of the mortar of the comparative example 4. And the shape retention and flexural strength of their extruded article were almost equivalent to those of the mortar of the comparative example 4 and superior to those of the mortar of the comparative example 5 (using a commercially available extruding auxiliary). It is obvious that the extruding auxiliaries according to the present invention are superior to the commercially available one with respect to the shape retention and strength of the extruded articles. Referring to the discharging pressure of mortar, the extruding auxiliaries according to the present invention were equivalent to the commercially available extruding auxiliary, accordingly, it is obvious that they have been improved in tackiness.

Examples 30 to 36, Comparative Examples 6 to 8

The extruding compositions of cement-based material were prepared in the same manner as in the examples 28 to 29 and comparative examples 4 to 5, except that the type of extruding auxiliaries, the amount of the same added, and the water/cement ratio were changed as shown in Table 5. The presence of water separation during extrusion, the surface topology and shape retention of the extruded articles, and the flexural strength of the extruded articles after curing were measured. The measured results are shown in Table 5.

TABLE 4

| Example No. | Type of Extruding Agent | Amount of Extruding Agent Added (% by weight per 100% by weight of cement) | Water/Cement Ratio | Discharging Pressure (kg/cm²) | Presence of Water Separation | Surface Topology | Shape Retention | Flexural Strength (kg/cm²) |
|---|---|---|---|---|---|---|---|---|
| Example 28 | Example 9 | 1.0 | 0.30 | 16 | ⊚ | ⊚ | ⊚ | 150 |
| Example 29 | Example 12 | 1.0 | 0.30 | 14 | ⊚ | ⊚ | ⊚ | 150 |
| Comparative Example 4 | Comparative Example 2 | 1.0 | 0.30 | 24 | ⊚ | ⊚ | ⊚ | 150 |
| Comparative Example 5 | Commercially Available Extruding Agent* | 1.0 | 0.30 | 17 | ⊚ | ⊚ | X | 130 |

*Metholose 90SH-30000 manufactured by Shin-Etsu Chemical Co., Ltd.

TABLE 5

| Example No. | Type of Extruding Agent | Amount of Extruding Agent Added (% by weight per 100% by weight of cement) | Water-Cement Ratio | Presence of Water Separation | Surface Topology | Shape Retention | Flexural Strength (kg/cm²) |
|---|---|---|---|---|---|---|---|
| Example 30 | Example 10 | 1.0 | 0.30 | ⊚ | ⊚ | ⊚ | 150 |
| Example 31 | Example 11 | 1.5 | 0.35 | ○ | ⊚ | ⊚ | 145 |
| Example 32 | Example 13 | 1.0 | 0.30 | ⊚ | ⊚ | ⊚ | 150 |
| Example 33 | Example 14 | 1.0 | 0.30 | ⊚ | ⊚ | ⊚ | 150 |
| Example 34 | Example 15 | 0.5 | 0.35 | ⊚ | ⊚ | ⊚ | 145 |
| Example 35 | Example 16 | 1.0 | 0.35 | ○ | ⊚ | ⊚ | 145 |
| Example 36 | Example 17 | 0.5 | 0.35 | ⊚ | ⊚ | ⊚ | 145 |
| Comparative Example 6 | Commercially Available Extruding Agent*1 | 1.5 | 0.35 | —*2 | — | — | — |
| Comparative | Commercially | 0.5 | 0.30 | ○ | ⊚ | X | 130 |

TABLE 5-continued

| Example No. | Type of Extruding Agent | Amount of Extruding Agent Added (% by weight per 100% by weight of cement) | Water-Cement Ratio | Presence of Water Separation | Surface Topology | Shape Retention | Flexural Strength (kg/cm$^2$) |
|---|---|---|---|---|---|---|---|
| Example 7 | Available Extruding Agent*[1] | | | | | | |
| Comparative Example 8 | No Extruding Agent Added | — | 0.35 | X*[3] | — | — | — |

*[1]Metholose 90SH-30000 manufactured by Shin-Etsu Chemical Co., Ltd.
*[2]The extrusion test was stopped because the mortar was foamed intensively in the vacuum defoaming chamber after the extrusion.
*[3]The extrusion test was stopped because water was separated from the mortar during the extrusion.

One of the characteristics of the extruding auxiliaries of the present invention is that their foamability is low, and therefore, their vacuum deaeration during extrusion is very effective.

(Examples of Mortar Production Using Mortar Thickening Agents)

In the following, examples of mortar production using the mortar thickening agents of the examples 24 to 27 and characteristics of the mortar produced will be described below; however, it should be understood that these examples are shown for illustrative purposes only and are not intended to limit the present invention.

Examples 37 to 40

Four different types of dry mortar were obtained by adding 400 g of portland cement, 400 g of standard sand and 1.6 g of each of the thickening agents of the example 24 to 27 into each mortar mixer and mixing them while stirring for 10 minutes.

180 g of water was added to this dry mortar (water-cement ratio 0.45) and mixed while stirring for 5 minutes, so as to thickened mortar.

The viscosity of this mortar at room temperature (21 to 22° C.) was measured with a rotating cylinder viscometer (Type B8M manufactured by TOKIMEC) at rotary speeds of the rotor of 0.6 to 60 rpm.

The compositions of the mortar are shown in Table 6 and the relationship between the viscosity of the mortar and the rotary speed of the rotor used for measurement are shown in FIG. 1.

Comparative Example 9

Mortar was prepared in the same manner as in the example 37, except that no thickening agent was added. And the viscosity of the mortar was measured in the same manner as in the example 37. The relationship between the viscosity of the mortar and the rotary speed of the rotor used for measurement are shown in FIG. 1.

Comparative Example 10

Mortar was produced in the same manner as in the example 37, except that instead of the thickening agent, the same amount of methyl cellulose was used. And the viscosity of the mortar was measured in the same manner as in the example 37. As the methyl cellulose, used was hi Metholose 90SH-15000 (2% aqueous solution viscosity 15,000 mPa·s) manufactured by Shin-Etsu Chemical Co., Ltd. and having almost the same 2% aqueous solution viscosity as the thickening agent produced in the example 24. The relationship between the viscosity of the mortar and the rotary speed of the rotor used for the measurement are shown in FIG. 1.

TABLE 6

| Type of Mortar | Cement (g) | Sand (g) | Thickening Agent Type | Amount (g) | Water |
|---|---|---|---|---|---|
| Example 37 | 400 | 400 | Example 24 | 1.6 | 180 |
| Example 38 | 400 | 400 | Example 25 | 1.6 | 180 |
| Example 39 | 400 | 400 | Example 26 | 1.6 | 180 |
| Example 40 | 400 | 400 | Example 27 | 1.6 | 180 |
| Comparative Example 9 | 400 | 400 | None | 0 | 180 |
| Comparative Example 10 | 400 | 400 | Metholose | 1.6 | 180 |

As shown in FIG. 1, in all the examples, the viscosity is decreased as the rotary speed becomes high. This phenomenon reflects the thixotropic properties of the mortar. It is obvious that the use of a thickening agent increased the viscosity of the mortar. The increase in viscosity at lower rotary speeds (lower shear force) serves to suppress the flow of mortar after placing and prevent sags from occurring. And the decrease in viscosity at higher rotary speeds (higher shear force) is a characteristic necessary for mortar to separate from a trowel satisfactorily.

The thickening agents produced in the example 24 and the comparative example 10 had almost the same thickening effect on mortar. Surprisingly, for the mortar using the thickening agents produced in the examples 25 and 26, it showed a high mortar viscosity equivalent to that of the mortar produced in the comparative example 10. It is obvious from these facts that the thickening agents of the present invention act very effectively in mortar.

The viscosity of mortar increases or decreases with the amount of the thickening agent added; accordingly, when using a thickening agent having a higher 2% aqueous solution viscosity, the thickening effect equivalent to that of the above examples can be developed by decreasing the amount of the thickening agent added.

As mortar thickening agents, various cellulose ethers differing in aqueous solution viscosity are used depending on their applications. However, it is obvious that, as long as the thickening agents of the present invention having a 2% aqueous solution viscosity in the range of 10 to 300,000 mPa·s are used in a suitable amount, in almost all the applications, currently used thickening agents such as methyl cellulose can be replaced with the thickening agents of the present invention.

(Setting Retardation of Mortar)

As a problem which arises when cellulose ethers are used as a thickening agents, it is widely known that the setting of mortar is retarded and the development of the initial strength of the mortar is also retarded. The present inventors examined the effects of the thickening agents according to the present invention on such setting retardation.

Example 41, Comparative Examples 11 to 12

The initial setting time of each mortar prepared in the example 37 and comparative examples 9 and 10 was measured with a Vicat needle apparatus manufactured by Maruto Corporation in accordance with JIS R 5201.

The mortar was packed into a container 40 mm deep, a predetermined initial needle was dropped on the mortar in a predetermined manner, the position at which the needle stopped was read using the graduations on the needle. The measurement was made at intervals of 30 minutes since the instance of adding water to the mortar. When the distance of the position at which the needle stopped from the bottom of the container was 1 mm or more, setting was considered to start, and the elapsed time since the instance of adding water to the mortar was defined as initial setting time. The difference from the initial setting time of the comparative example 9 was defined as setting retardation time. The presence of water bleeding on the mortar surface was checked by visual observation 3 hours after the addition of water to the mortar. The results are shown in Table 7.

TABLE 7

| Example No. | Type of Mortar | Initial Setting Time (hour) | Setting Retardation Time (hour) | Bleeding |
|---|---|---|---|---|
| Example 41 | Example 37 | 6.0 | 2.5 | Absent |
| Comparative Example 11 | Comparative Example 9 | 3.5 | 0 | Present |
| Comparative Example 12 | Comparative Example 10 | 8.0 | 4.5 | Absent |

As can be seen from Table 7, for the mortar of the example 37, its retardation of setting is shorter than that of the mortar of the comparative example 10 and the phenomenon of bleeding, which is observed in the mortar of the comparative example 9, is satisfactorily suppressed.

It is obvious that the thickening agents of the present invention have the thickening effect equivalent to that of the commercially available thickening agents and impart to mortar thixotropic properties and water retention necessary for placing thereof, though their retardation of setting is shorter than the commercially available thickening agents.
(Comparison of Solubility with Mortar Thickening Agent Using Other Type Comb-shaped Hydrophobic Diol)

Example 42 and Comparative Example 13

A comparison was made between the speed of dissolving in mortar of the thickening agent obtained in the comparative example 3 in mortar and that of the thickening agent obtained in the example 24. The comparison was made in such a manner that the mortar having the same composition as that of the example 37 (the example 42) and the mortar having the same composition as that of the example 37 except that the thickening agent was replaced with that of the comparative example 3 (the comparative example 13) were mixed with respective mixers for 5 minutes while the time elapsed before the mortar was thickened and kept in a almost constant state was measured with a stopwatch.

As a result, in the comparative example 13, it took about 3 minutes to dissolve the thickening agent of the comparative example 3 in mortar while in the example 42, the thickening agent of the example 24 was almost dissolved in mortar in a minute and the mortar was kept in a constant state.

Taking into account the fact that the 2% aqueous solution viscosity and particle diameter of the two thickening agents are almost the same, it can be said that the solubility of the polymer itself in mortar was improved.
(Measurement of Setting Retardation Time on Underwater Concrete Using Underwater Concrete Thickening Agent)

The setting retardation time of underwater concrete using the water-soluble polyurethane obtained in the examples 12, 15 and 16 was measured and the measurements were compared with that of the commercially available cellulose ether. It should be understood that these examples are shown for illustrative purposes only and are not intended to limit the present invention.

Examples 43 to 45, Comparative Examples 14 to 15

The measurement was made on cement paste and mortar; however, since the measured results were almost the same in both cases, the results of the cement paste only will be shown below. The measurement was made in such a manner that a predetermined amount of thickening agent powder consisting of the water-soluble polyurethane obtained in the example 15, 12 or 16 or the commercially available cellulose ether (Metholose 90SH-30000 manufactured by Shin-Etsu Chemical Co., Ltd.) was added to and mixed with 100 g of ordinary portland cement, then 40 g of water was added and fully mixed, so as to obtain cement paste, the cement paste thus obtained was packed into a cylindrical insulating container, a thermocouple was inserted into the container around its center portion, and the variation of the internal temperature of the cement paste with time was recorded. This recorded variation was compared with that of the cement paste with no thickening agent added thereto. The results are shown in Table 8.

TABLE 8

| Example No. | Type of Thickening Agent | Amount of Thickening Agent Added (% by weight per 100% by weight of cement) | Temperature at Peak of Heat Releasing (° C.) | Elapsed Time at Peak of Heat Releasing (hr) | Setting Retardation Time (hr) |
|---|---|---|---|---|---|
| Comparative Example 14 | None | — | 50 | 9.5 | 0 |
| Example 43 | Example 15 | 0.1 | 50 | 9.5 | 0 |
| Example 44 | Example 12 | 1 | 52 | 9.7 | 0.2 |
| Example 45 | Example 16 | 10 | 52 | 10.0 | 0.5 |

TABLE 8-continued

| Example No. | Type of Thickening Agent | Amount of Thickening Agent Added (% by weight per 100% by weight of cement) | Temperature at Peak of Heat Releasing (° C.) | Elapsed Time at Peak of Heat Releasing (hr) | Setting Retardation Time (hr) |
|---|---|---|---|---|---|
| Comparative Example 15 | Commercially Available Thickening Agent* | 1 | 44 | 16.5 | 7.0 |

*Metholose 90SH-30000 manufactured by Shin-Etsu Chemical Co., Ltd.

As can be seen from Table 8, retardation of setting occurred in the cement paste using Metholose, which is a commercially available thickening agent, while it did not substantially occur in the cement paste using the thickening agents of the present invention. It is widely known that cellulose ethers cause setting retardation of cement, and the reason is generally considered to be the existence of a large number of hydroxyl groups on the polymer main chain. It is considered to be that, when there exist a large number of strong polar groups such as hydroxyl groups in a polymer, the polymer tends to bond strongly to calcium of the cement and the cement runs short of calcium content necessary for hydration reaction.

On the other hand the reasons that, in the cement paste using the underwater concrete thickening agent of the present invention, retardation of setting is not caused are not fully clarified yet; however, it is considered one of the reasons may be that ether groups as hydrophilic groups of the polymer main chain have relatively weak polarity and these groups do not bond to calcium strongly, accordingly, retardation of setting is not caused.

(Underwater Concrete Placing Test)

Tests were conducted using concrete consisting of cement, sand, gravel, a thickening agent and water.

Examples 46 to 51, Comparative Examples 16 to 18

100 parts by weight of ordinary portland cement, 180 parts by weight of sand, 250 parts by weight of gravel and a predetermined amount of thickening agent consisting of water-soluble polyurethane of the example 15, 12 or 16 were mixed with a concrete mixer. Then, 50 parts by weight of water was added to this composition, and further mixed, so as to obtain an underwater concrete composition. This concrete was allowed to freely fall underwater and packed into a cylindrical form 10 cm in diameter and 20 cm high sunk into a pool 1 m deep. After 24 hours, this specimen was taken out of the water to remove the form and subjected to underwater curing, and its $7^{th}$ day strength and $28^{th}$ day strength were measured. And the presence of aggregate separation inside the specimen was observed.

For comparison, two other examples are shown: one in which the commercially available typical cellulose ether thickening agent, methyl cellulose, 90SH-30000 manufactured by Shin-Etsu Chemical Co., Ltd. was used and the other one in which no thickening agent was used.

Table 9 shows the type of the thickening agents used in the examples and comparative examples, the amount of the same (% by weight per 100% by weight of cement), the water/cement ratio (W/C), the underwater anti-separation properties (capability of not allowing the aggregate to separate underwater) and the compressive strength after curing.

The presence of the aggregate separation was judged by observing the specimen before and after the measurement of the compressive strength. When observing no aggregate separation, the condition was judged to be good (⊚) When observing a little aggregate separation, but it was not so remarkable, the condition was judged to be fair (○). And when observing clear aggregate separation, the condition was judged to be failure (x).

TABLE 9

| Example No. | Type of Thickening Agent | 2% Aqueous Solution Viscosity (mPa · s) | Amount of Thickening Agent Added (% by weight per 100% by weight cement) | Underwater Anti-separation Properties | 7th Day Strength (kg/cm$^2$) | 28th Day Strength (kg/cm$^2$) |
|---|---|---|---|---|---|---|
| Example 46 | Example 12 | 50,000 | 1.0 | ⊚ | 240 | 350 |
| Example 47 | Example 12 | 50,000 | 5.0 | ⊚ | 250 | 360 |
| Example 48 | Example 15 | 500,000 | 0.1 | ○ | 240 | 340 |
| Example 49 | Example 15 | 500,000 | 0.2 | ⊚ | 250 | 370 |
| Example 50 | Example 15 | 500,000 | 0.5 | ⊚ | 230 | 360 |
| Example 51 | Example 16 | 1,000 | 10.0 | ⊚ | 230 | 340 |
| Comparative Example 16 | Commercially Available Thickening Agent* | 30,000 | 1.0 | ⊚ | 150 | 250 |
| Comparative Example 17 | Commercially Available Thickening Agent* | 30,000 | 0.1 | X | — | — |
| Comparative Example 18 | No Thickening Agent Added | — | — | X | — | — |

*Metholose 90SH-30000 manufactured by Shin-Etsu Chemical Co., Ltd.

Comparing the examples and the comparative examples, it is obvious that the underwater concrete thickening agents according to the present invention have underwater anti-separation properties at least equivalent to and strength superior to the commercially available thickening agents (water-soluble cellulose ethers).

The underwater anti-separation properties may reflect the excellent thixotropic properties of the concrete. The reason is not fully clear; however, it is considered that the excellent thixotropic properties of the concrete (underwater concrete composition) according to the present invention reflect not only the high viscosity of the polyurethane aqueous solution, but also the effects of the moderate interactions between the comb-shaped hydrophobic group of the water-soluble polyurethane and the cement particles.

For the strength after curing, the concrete of the present invention is particularly superior in initial strength to the concrete using the commercially available thickening agents. This may be because the concrete of the present invention does not cause retardation of setting.

(Extrusion of Ceramics)

In the following, examples of ceramics extrusion binder production using the water-soluble polyurethane of the examples 9 and 12 and the characteristics of the products are described; however, it should be understood that these examples are shown for illustrative purposes only and are not intended to limit the present invention.

Examples 52 to 53, Comparative Examples 19 to 21

Examples are shown in which the composition of alumina green sand with the binder of the present invention was used as a ceramics forming binder. And comparative examples are shown in which hydroxypropyl methyl cellulose (HPMC) was used as a binder.

The composition used in the tests was as follows:

| | |
|---|---|
| Alumina | 100 parts by weight |
| Glycerol | 2 parts by weight |
| Binder | a predetermined amount shown in Table |
| Water | 20 parts by weight |

As a prior art binder, used was HPMC (Metholose 60SH-4000).

These compositions were extruded with a vacuum extruding machine (Miyazaki Iron Works Co., Ltd., FM-30) into plate-shaped articles 2 cm wide and 1 cm thick, and their formability was evaluated. The mark ○ indicates that extrusion is smoothly carried out and the surface topology of extruded articles is good, the mark Δ indicates that the surface topology of extruded articles is a little rough and the mark x indicates that the surface topology of extruded articles is rough or extrusion cannot be carried out.

The extruded articles were subjected to temporary calcination in the air at 500° C. The state where none of the 20 test pieces cracked in this calcination was expressed as ○, the state where 1 to 2 test pieces cracked was expressed as Δ, and the state where 3 or more test pieces cracked was expressed as x. The results are shown in Table 10.

TABLE 10

| Example No. | Type of Binder | Amount of Binder Added (part by weight) | Formability | Yield after Temporary Calcination |
|---|---|---|---|---|
| Example 52 | Example 9 | 2.0 | ○ | ○ |
| Example 53 | Example 12 | 2.0 | ○ | ○ |
| Comparative Example 19 | HPMC | 4.0 | ○ | x |
| Comparative Example 20 | HPMC | 2.0 | Δ | Δ |
| Comparative Example 21 | No Binder Added | — | x | —* |

*The formability of the composition was bad and it could not be subjected to temporary calcination.

As can be seen from Table 10, with respect to formability of alumina green sand, the compositions using the binders of the present invention have the formability equivalent to that of the compositions using the currently used binder. And the use of the binders of the present invention greatly improves the yield of the products in a calcination step.

(Thermal Analysis of Binder)

The improvement in the yield of products in a calcination step is related with the pyrolytic behavior of the binders. Accordingly, the pyrolytic behavior of the binders was evaluated by the TGA (thermmogravimetric analysis) and the DTA (differential thermal analysis).

Example 54 and Comparative Example 22

Figure 2A:
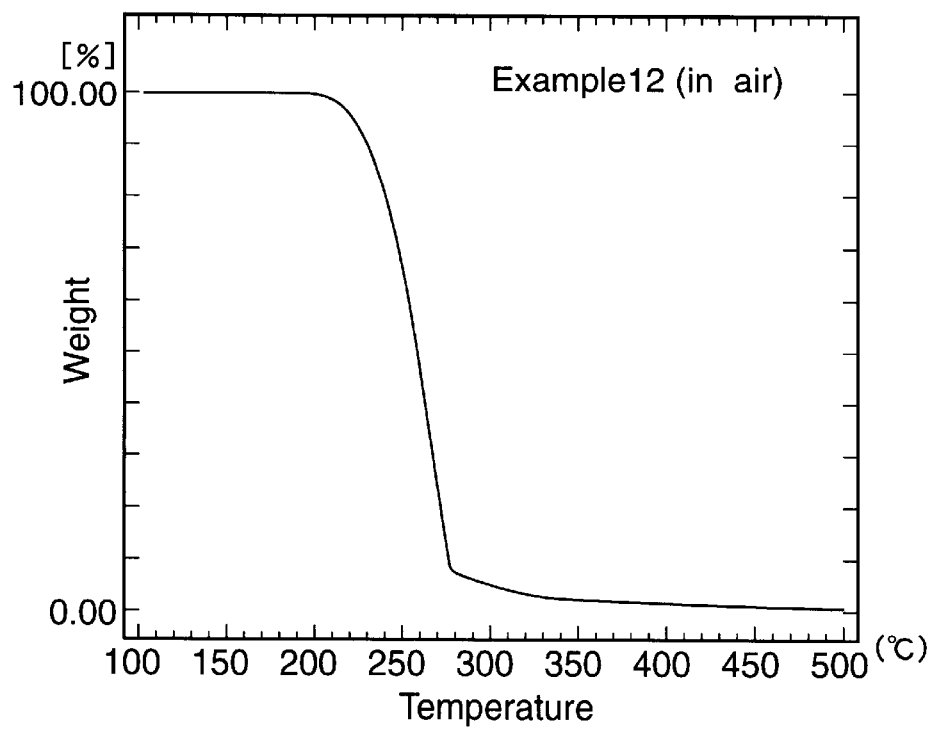
Figure 2A:
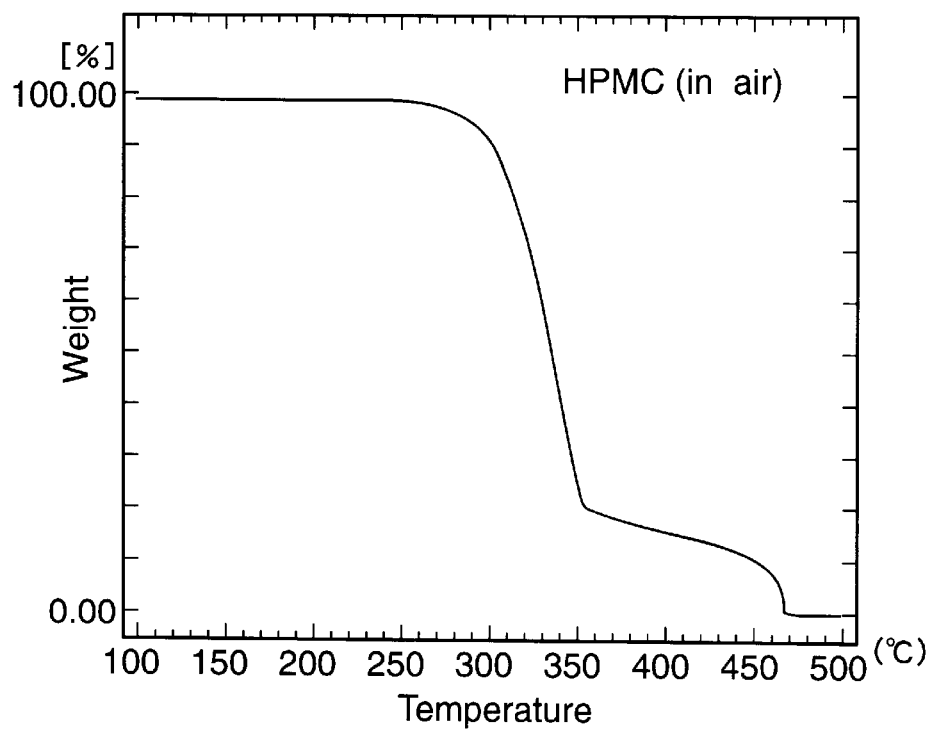
Figure 3A:
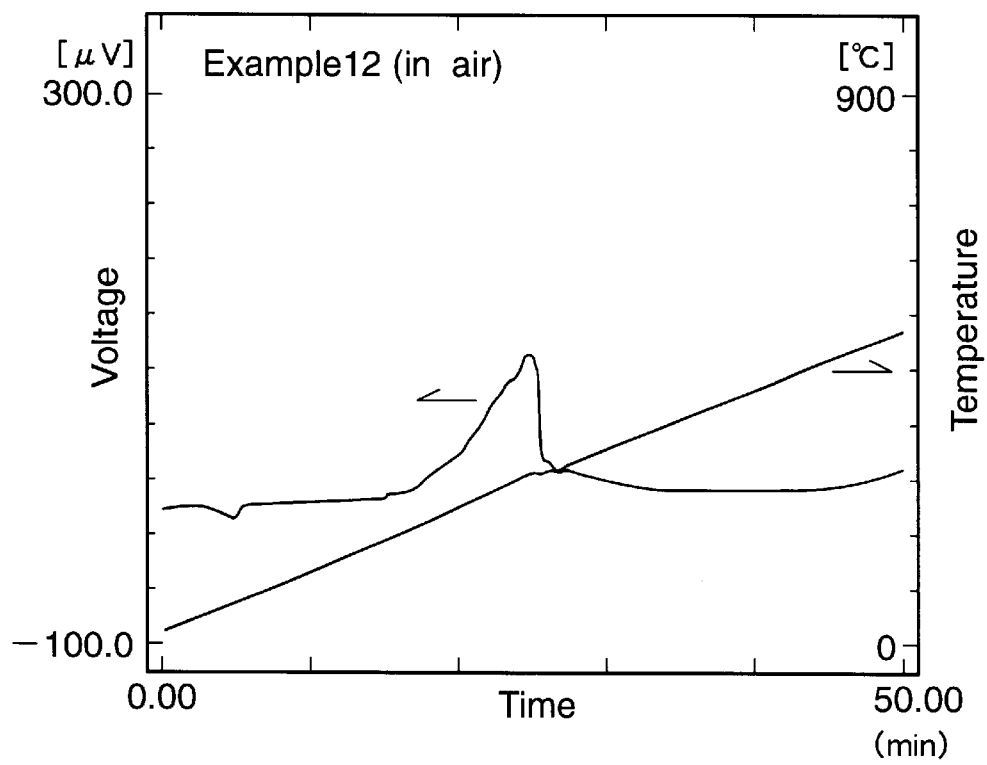
FIG. 3a is a graphical view showing the result of DTA (differential thermal analysis) measurements for the thermal decomposition behavior of a binder according to the present invention.
Figure 3B:
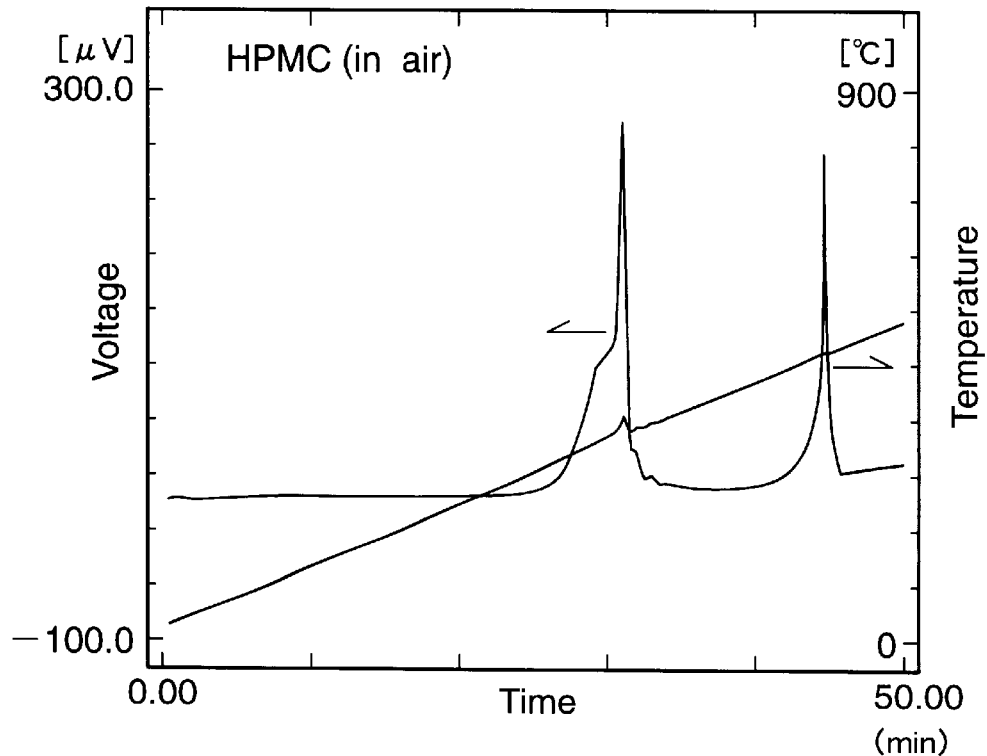
FIG. 3b is a graphical view showing the result of DTA (differential thermal analysis) measurement of the thermal decomposition behavior for a conventional binder.

The pyrolytic behavior of the water-soluble polyurethane obtained in the example 12 and the prior art binder, hydroxypropyl methyl cellulose, were evaluated by the TGA (thermmogravimetric analysis) and the DTA (differential thermal analysis). FIGS. 2a and 2b show the measurements by the TGA and FIGS. 3a and 3b show the measurements by the DTA.

FIG. 2a and FIG. 2b show the TGA measurements of the binder of the present invention and the prior art binder, hydroxypropyl methyl cellulose, respectively. The measurement was carried out in the air at a heating rate of 10° C./min. Table 11 shows the carbon residue content at 500° C. and the temperature at which the weight of the binders is decreased by 5% (Td5) as the thermal decomposition initiating temperature. Table 11 also shows the measurements in nitrogen.

TABLE 11

| | | In Air (10° C./min) | | In Nitrogen (10° C./min) | |
|---|---|---|---|---|---|
| Example No. | Type of Binder | Td5 (° C.) | Carbon Residue Content (%) | Td5 (° C.) | Carbon Residue Content (%) |
| Example 54 | Example 12 | 228 | <1 | 372 | 1.5 |
| Comparative Example 22 | HPMC | 298 | <1 | 336 | 12 |

Table 11 shows that the binder of the present invention begins to be decomposed at low temperatures compared with the currently used binder and its carbon residue content is low, accordingly, degreasing can be carried out more effectively with the binder of the present invention.

FIGS. 3a and 3b show the DTA measurements of the binder of the present invention and the prior art binder, hydroxypropyl methyl cellulose, respectively. The measurement was carried out in air at a heating rate of 10° C./min. The area of DTA curve is proportional to the heat value, and the calorific value of the binder of the present invention was 68% as high as that of the prior art binder (HPMC).

It is obvious that in the binder of the present invention, compared with the prior art binder, its heat release is moderate and its relative heat value is low, accordingly, the occurrence of thermal distortion in the extruded articles during the degreasing step (temporary calcination step) is a little.

It is clear from the above tests that the pyrolytic behavior of the binder of the present invention is moderate compared with the prior art binder, accordingly, the binder of the present invention contributes to the improvement in the yield of extruded articles during calcination, and hence, in productivity. Due to the moderate heat release and small heat value, the temperature of the extruded articles during calcination has a narrow distribution, which prevents thermal failure of the extruded articles. Further, since the heating rate can be increased, the productivity is improved.

(Hair Conditioners)

Examples of hair conditioners are shown below in which the water soluble polyurethanes of the present invention are used as moisturizers for use in hair cosmetics; however, it should be understood that these examples are shown for illustrative purposes only and are not intended to limit the present invention.

Examples 55 to 57, Comparative Examples 23 to 25

The composition used in the tests are as follows.

Trimethyl anmonium stearyl chloride 1% by weight
Propylene Glycol 5% by weight
Cetyl alcohol 2% by weight
Oleyl alcohol EO addition product 0.5% by weight
Moisturizer predetermined amount shown in Table 12
Perfume proper amount
Preservatives proper amount
Purified water rest
Total 100% by weight As moisturizers, used were the water-soluble polyurethane obtained in the examples 9, 20 and 24. For comparison, examples are shown in which polyethylene glycol (PEG) and hydroxyethyl cellulose (HEC) were used as moisturizers and no moisturizer was added.

The feel of hair (moist feel) treated with the above composition was evaluated. The mark ⊚ indicates that the moist feel was very satisfactory, the mark ○ satisfactory and the mark x bad. The evaluation is based on the replies of ten male and female collaborators selected by random sampling. The results are shown in Table 12.

TABLE 12

| Example No. | Type of Moisturizer | Amount of Moisturizer Added (% by weight) | Moist Feel after Drying | Remarks |
| --- | --- | --- | --- | --- |
| Example 55 | Example 9 | 1.0 | ⊚ | |
| Example 56 | Example 20 | 1.0 | ⊚ | |
| Example 57 | Example 24 | 1.0 | ○ | |
| Comparative | PEG | 1.5 | x | Oily |

TABLE 12-continued

| Example No. | Type of Moisturizer | Amount of Moisturizer Added (% by weight) | Moist Feel after Drying | Remarks |
| --- | --- | --- | --- | --- |
| Example 23 | | | | feel |
| Comparative Example 24 | HEC | 1.0 | x | Dry feel |
| Comparative Example 25 | No Moisturizer Added | — | x | |

The moisturizer of the comparative examples could not impart satisfactory moist feel to hair, but oily feel or dry feel. On the other hand, the moisturizer of the present invention could impart soft feel to hair, neither oily feel nor dry feel.

What is claimed is:

1. A comb-shaped diol represented by the following general formula (1b):

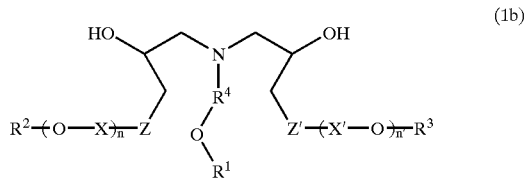

(1b)

wherein $R^1$ is a hydrocarbon group of 1 to 20 carbon atoms; each of $R^2$ and $R^3$ is a hydrocarbon group of 4 to 21 carbon atoms; some or all of the hydrogen atoms of the hydrocarbon groups $R^1$, $R^2$ and $R^3$ may be substituted with fluorine, chlorine, bromine or iodine; $R^2$ and $R^3$ may be the same or different from each other; each of X, X' and X" is an alkylene group of 2 to 10 carbon atoms; X, X' and X" may be the same or different from each other; some of the hydrogen atoms of the above alkylene group may be substituted with an alkyl group, chlorine or an alkyl chloride group; each of Z and Z' is oxygen, sulfur or a $CH_2$ group; Z and Z' may be the same or different from each other; $R^4$ is an alkylene group of 2 to 10 carbon atoms in all; n is an integer of 0 to 15 when Z is oxygen and is 0 when Z is sulfur or a $CH_2$ group; n' is an integer of 0 to 15 when Z' is oxygen and is 0 when Z' is sulfur or a $CH_2$ group; and n and n' may be the same or different from each other.

2. The comb-shaped diol as claimed in claim 1, wherein said comb-shaped diol is represented by the following general formula (1c):

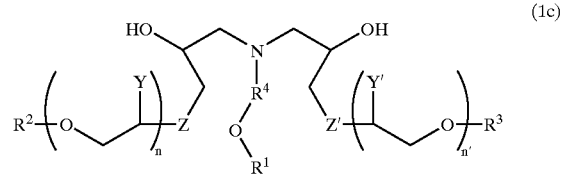

(1c)

wherein $R^1$ is a hydrocarbon group of 1 to 20 carbon atoms; each of $R^2$ and $R^3$ is a hydrocarbon group of 4 to 21 carbon atoms; some or all of the hydrogen atoms of the hydrocarbon groups $R^1$, $R^2$ and $R^3$ may be substituted with fluorine, chlorine, bromine or iodine; $R^2$ and $R^3$ may be the same or different from each other; each of Y, Y' and Y" is hydrogen, a methyl group or a $CH_2Cl$ group; Y and Y' may be the same or different from each other; each of Z and Z' is oxygen, sulfur or a $CH_2$ group; Z and Z' may be the same or different from each other; $R^4$ is an alkylene group of 2 to 4 carbon atoms in all; n is an integer of 0 to 15 when Z is oxygen and is 0 when Z is sulfur or a $CH_2$ group; n' is an integer of 0 to 15 when Z' is oxygen and is 0 when Z' is sulfur or a $CH_2$ group; and n and n' may be the same or different from each other.

3. The comb-shaped diol as claimed in claim 1, wherein said comb-shaped diol is represented by the following general formula (2):

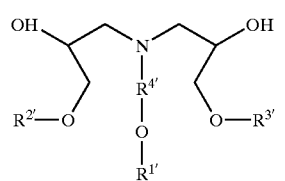

(2)

wherein $R^{1'}$ is an alkyl group of 1 to 18 carbon atoms; each of $R^{2'}$ and $R^{3'}$ is a hydrocarbon group of 4 to 21 carbon atoms; $R^{2'}$ and $R^{3'}$ are the same; $R^4$ is a 1,2-ethylene group, 1,3-propylene group or 1,4-butylene group.

4. Water-soluble polyurethane comprising a polymer having a repeating unit (U-1) represented by the following general formula (3):

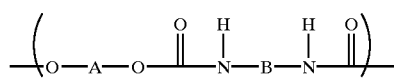

(3)

and a repeating unit (U-2) represented by the following general formula (4):

(4)

wherein A is a bivalent group derived from a water-soluble polyalkylene polyol having the general formula HO—A—OH, having hydroxyl groups at least on both terminals thereof and having a number average molecular weight of 400 to 100,000; B is a bivalent group derived from a polyisocyanate compound selected from the group consisting of polyisocyanates represented by the general formula OCN—B—NCO and having 3 to 18 carbon atoms; and D is a bivalent group such that the compounds having the general formula HO—D—OH are comb-shaped hydrophobic diol represented by the following general formula (1):

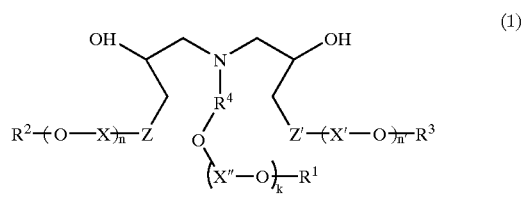

(1)

wherein $R^1$ is a hydrocarbon group of 1 to 20 carbon toms; each of $R^2$ and $R^3$ is a hydrocarbon group of 4 to 21 carbon atoms; some or all of the hydrogen atoms of the hydrocarbon groups $R^1$, $R^2$ and $R^3$ may be substituted with fluorine, chlorine, bromine or iodine; $R^2$ and $R^3$ may be the same or different from each other; each of X, X' and X" is an alkylene group of 2 to 10 carbon atoms; X, X' and X" may be the same or different from each other; some of the hydrogen atoms of the above alkylene group may be substituted with an alkyl group, chlorine or an alkyl chloride group; each of Z and Z' is oxygen, sulfur or a $CH_2$ group; Z and Z' may be the same or different from each other; $R^4$ is an alkylene group of 2 to 10 carbon atoms in all; k is an integer of 0 to 15; n is an integer of 0 to 15 when Z is oxygen and is 0 when Z is sulfur or a $CH_2$ group; n' is an integer of 0 to 15 when Z' is oxygen and is 0 when Z' is sulfur or a $CH_2$ group; and n and n' may be the same or different from each other, wherein the molar ratio of the repeating unit (U-1) is 0.5 or higher and 0.999 or lower, the molar ratio of the repeating unit (U-2) is 0.001 or higher and 0.5 or lower, and that the weight average molecular weight measured by the GPC is in the range of 10,000 to 10,000,000.

5. The water-soluble polyurethane as claimed in claim 4, wherein said comb-shaped diol has the following general formula (1a):

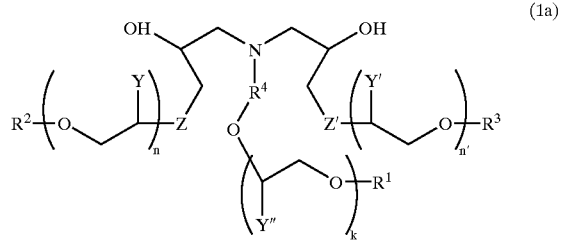

(1a)

wherein $R^1$ is a hydrocarbon group of 1 to 20 carbon atoms; each of $R^2$ and $R^3$ is a hydrocarbon group of 4 to 21 carbon atoms; some or all of the hydrogen atoms of the hydrocarbon groups $R^1$, $R^2$ and $R^3$ may be substituted with fluorine, chlorine, bromine or iodine; $R^2$ and $R^3$ may be the same or different from each other; each of Y, Y' and Y" is hydrogen, a methyl group or a $CH_2Cl$ group; Y and Y' may be the same or different from each other; each of Z and Z' is oxygen, sulfur or a $CH_2$ group; Z and Z' may be the same or different from each other; R' is an alkylene group of 2 to 4 carbon atoms in all; k is an integer of 0 to 15; n is an integer of 0 to 15 when Z is oxygen and is 0 when Z is sulfur or a $CH_2$ group; n' is an integer of 0 to 15 when Z' is oxygen and is 0 when Z' is sulfur or a $CH_2$ group; and n and n' may be the same or different from each other.

6. The water-soluble polyurethane as claimed in claim 4, wherein said comb-shaped diol has the following general formula (2):

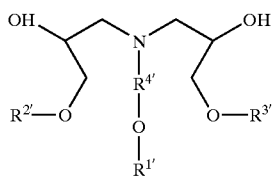

wherein $R^{1'}$ is an alkyl group of 1 to 18 carbon atoms; each of $R^{2'}$ and $R^{3'}$ is a hydrocarbon group of 4 to 21 carbon atoms; $R^{2'}$ and $R^{3'}$ are the same; $R^4$ is a 1,2-ethylene group, 1,3-propylene group or 1,4-butylene group.

7. The water-soluble polyurethane as claimed in claim 4, wherein the molar ratio of the repeating unit (U-1) is 0.5 or higher and 0.99 or lower, the molar ratio of the repeating unit (U-2) is 0.01 or higher and 0.5 or lower, the water-soluble polyalkylene polyol is polyethylene glycol of which number average molecular weight is 3,000 to 20,000, the polyisocyanate compound is a diisocyanate compound selected from the group consisting of aliphatic diisocyanates of which total number of carbon atoms is 3 to 18, the comb-shaped diol is the comb-shaped diol having the following general formula (2):

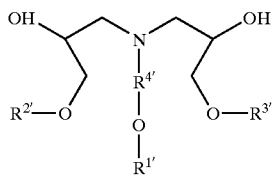

wherein $R^1$ is an alkyl group of 1 to 18 carbon atoms; each of $R^{2'}$ and $R^{3'}$ is a hydrocarbon group of 4 to 21 carbon atoms; $R^{2'}$ and $R^{3'}$ are the same; $R^{4'}$ is a 1,2-ethylene group, 1,3-propylene group or 1,4-butylene group, and that the weight average molecular weight of said polyurethane measured by the GPC is in the range of 100,000 to 1,000,000.

8. The water-soluble polyurethane according to one of claims 4 to 7, wherein the polyisocyanate compound is a compound selected from the group consisting of hexamethylene diisocyanate, isophoronediisocyanate, hydrogenated xylylenediisocyanate, hydrogenated tolylenediisocyanate or norbornanediisocyanatomethyl.

9. An extruding auxiliary for use in cement-based materials, comprising the water-soluble polyurethane according to claim 4.

10. The extruding auxiliary for use in cement-based materials as claimed in claim 9, wherein 2.5% aqueous solution of said water-soluble polyurethane has a viscosity being in the range of 1,000 to 1,000,000 mPa·s.

11. An extruding composition of cement-based material comprising the extruding auxiliary as claimed in claim 9 or 10, a hydraulic inorganic powder, a fine aggregate, a fiber and water.

12. The extruding composition of cement-based material as claimed in claim 11, wherein said fiber is an asbestos-substitute fiber.

13. An extruded article of cement-based material, which is obtained by extruding the extruding composition of cement-based material as claimed in claim 11.

14. A mortar thickening agent, comprising the water-soluble polyurethane according to one of claims 4 to 6.

15. The mortar thickening agent as claimed in claim 14, wherein said water-soluble polyurethane is that the molar ratio of the repeating unit (U-1) represented by the general formula (3) is 0.5 or higher and 0.99 or lower, the molar ratio of the repeating unit (U-2) represented by the general formula (4) is 0.01 or higher and 0.5 or lower, and wherein 2% aqueous solution of said water-soluble polyurethane has a viscosity being in the range of 10 mPa·s to 300,000 mPa·s at 20° C.

16. The mortar thickening agent as claimed in claim 14, wherein said water-soluble polyalkylene polyol is polyethylene glycol of which number average molecular weight is in the range of 1,000 to 20,000.

17. The mortar thickening agent according to claim 14, wherein said polyisocyanate compound is a chain aliphatic diisocyanate or cyclic aliphatic diisocyanate.

18. The mortar thickening agent according to claim 14, wherein said polyisocyanate compound is a compound selected from the group consisting of hexamethylene diisocyanate, isophoronediisocyanate, hydrogenated tolylenediisocyanate, hydrogenated xylylenediisocyanate, and norbornanediisocyanatomethyl.

19. A dry mortar composition, comprising the mortar thickening agent according to claim 14 and a hydraulic inorganic powder.

20. A mortar composition, comprising the mortar thickening agent according to claim 14, a hydraulic inorganic powder and water.

21. A thickening agent for underwater concrete, comprising the water-soluble polyurethane according to one of claims 4 to 6.

22. The thickening agent for underwater concrete as claimed in claim 21, wherein said water-soluble polyurethane is that the molar ratio of the repeating unit (U-1) represented the general formula (3) is 0.5 or higher and 0.99 or lower, the molar ratio of the repeating unit (U-2) represented by the general formula (4) is 0.01 or higher and 0.5 or lower, and wherein said water-soluble polyurethane has a weight average molecular weight measured by the GPC being in the range of 100,000 to 1,000,000.

23. The thickening agent for underwater concrete as claimed in claim 21, wherein said polyisocyanate compound is a chain aliphatic diisocyanate or cyclic aliphatic diisocyanate.

24. The thickening agent for underwater concrete according to claim 21, wherein the polyisocyanate compound is a compound selected from the group consisting of hexamethylene diisocyanate, isophoronediisocyanate, hydrogenated tolylenediisocyanate, hydrogenated xylylenediisocyanate, and norbornanediisocyanatomethyl.

25. The underwater concrete thickening agent according to one of claims 21 to 24, wherein 2% aqueous solution of said water-soluble polyurethane has a viscosity being in the range of 1,000 to 500,000 mPa·s.

26. An underwater concrete composition, which comprises cement and the thickening agent as claimed in claim 21, wherein said thickening agent is added at a rate of 0.1 to 10% by weight on the basis of 100% by weight of said cement.

27. A ceramics forming binder, which comprises the water-soluble polyurethane according to one of claims 4 to 6.

28. The ceramics forming binder as claimed in claim 27, wherein said water-soluble polyurethane is that the molar ratio of the repeating unit (U-1) represented by the general formula (3) is 0.5 or higher and 0.99 or lower, the molar ratio of the repeating unit (U-2) represented by the general formula (4) is 0.01 or higher and 0.5 or lower, and wherein said water-soluble polyurethane has a weight average molecular weight measured by the GPC being in the range of 10,000 to 1,000,000.

29. The ceramics forming binder as claimed in claim 27, wherein said water-soluble polyalkylene polyol is polyethylene glycol having a number average molecular weight of 1,000 to 20,000 and said polyisocyanate compound is a chain aliphatic diisocyanate or cyclic aliphatic diisocyanate.

30. The ceramics forming binder according to claim 27, wherein said polyisocyanate compound is a compound selected from the group consisting of hexamethylene diisocyanate, isophoronediisocyanate, hydrogenated tolylenediisocyanate, hydrogenated xylylenediisocyanate, and norbornanediisocyanatomethyl.

31. The ceramics forming binder according to claim 27, wherein said binder is used as a binder for ceramics extrusion.

32. A moisturizer for use in hair cosmetics, which comprises the water-soluble polyurethane according to one of claims 4 to 6.

33. The moisturizer for use in hair cosmetics as claimed in claim 32, wherein said water-soluble polyurethane is that the molar ratio of the repeating unit (U-1) represented by the general formula (3) is 0.5 or higher and 0.99 or lower, the molar ratio of the repeating unit (U-2) represented by the general formula (4) is 0.01 or higher and 0.5 or lower, and wherein said water-soluble polyurethane has a weight average molecular weight measured by the GPC being in the range of 10,000 to 1,000,000.

34. The moisturizer for use in hair cosmetics as claimed in claim 32, wherein said water-soluble polyalkylene polyol is polyethylene glycol having a number average molecular weight of 400 to 20,000 and said polyisocyanate compound is a chain aliphatic diisocyanate or cyclic aliphatic diisocyanate.

35. The moisturizer for use in hair cosmetics according to claim 32, wherein said polyisocyanate compound is a compound selected from the group consisting of hexamethylene diisocyanate, isophoronediisocyanate, hydrogenated tolylenediisocyanate, hydrogenated xylylenediisocyanate, and norbornanediisocyanatomethyl.

* * * * *